United States Patent [19]

Buckle et al.

[11] 4,427,686
[45] Jan. 24, 1984

[54] PHARMACOLOGICALLY ACTIVE BENZOPYRANOTRIAZOLE COMPOUNDS

[75] Inventors: Derek R. Buckle, Redhill; Harry Smith, Maplehurst Nr Horsham, both of England

[73] Assignee: Beecham Group Limited, England

[21] Appl. No.: 328,732

[22] Filed: Dec. 8, 1981

[30] Foreign Application Priority Data

Dec. 13, 1980 [GB] United Kingdom ............... 8040020
Mar. 26, 1981 [GB] United Kingdom ............... 8109551

[51] Int. Cl.³ .................. A61K 31/41; C07D 491/052
[52] U.S. Cl. ................................ 424/269; 260/456 R; 260/456 P; 424/245; 548/101; 548/255; 548/256; 549/554; 549/560; 568/337; 568/572; 568/644; 568/650
[58] Field of Search ............... 548/101, 256; 424/245, 424/269

[56] References Cited

U.S. PATENT DOCUMENTS 4,248,879 2/1981 Buckle et al. ...................... 424/269

FOREIGN PATENT DOCUMENTS 7727 2/1980 European Pat. Off. ............ 424/269
32821 7/1981 European Pat. Off. ............ 424/269

Primary Examiner—Alton D. Rollins
Attorney, Agent, or Firm—Jacobs & Jacobs

[57] ABSTRACT

A compound of the formula (I):

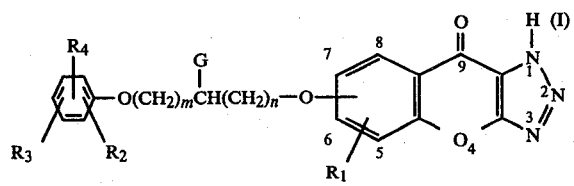

wherein
$R_1$ is hydrogen or $C_{1-6}$ alkyl;
$R_2$, $R_3$ and $R_4$ are the same or different and are chosen from hydrogen, hydroxyl, halogen, $C_{1-4}$ alkyl, $C_{1-4}$ alkoxy and $C_{1-4}$ alkanoyl;
G is H or OH; and
m and n are independently 1 to 3; with the proviso that when G is OH, one of m or n is 1; is useful in the prophylaxis and treatment of diseases whose symptoms are controlled by the mediators of the allergic response, for example asthma, hay fever, rhinitis and allergic eczema.

11 Claims, No Drawings

PHARMACOLOGICALLY ACTIVE BENZOPYRANOTRIAZOLE COMPOUNDS

This invention relates to novel compounds, pharmaceutical compositions containing them, their formulation into pharmaceutical compositions, their use in therapy of allergy, and a process for their preparation.

It is known that some types of cells, such as mast cells, are activated by antibody-antigen combination and release substances (mediators) which mediate the allergic response. It has been reported that SRS-A (the slow reacting substance of anaphylaxis) is one such mediator, and when released from such cells under activation by antibody-antigen combinations, plays an important role in the development of allergic and asthmatic phenomena.

The compound FPL 55712:

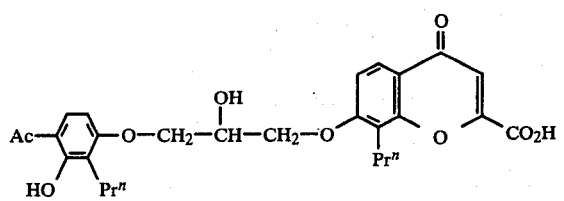

is a known compound which is able to effect at least some inhibition of release of these allergic response mediators, and also to inhibit released SRS-A.

It is also known that certain substituted cyano- and nitro- hydroxycoumarins and -indandiones can inhibit release of these mediators and inhibit released SRS-A. Examples of such compounds are those described in U.K. Pat. No. 1,555,753, of formula (A):

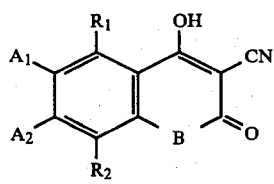

and pharmaceutically acceptable salts thereof wherein B is an oxygen atom or a covalent bond; $R_1$, $R_2$ and one of $A_1$ and $A_2$ are each hydrogen or lower alkyl, and the other one of $A_1$ and $A_2$ is of formula

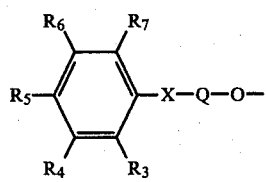

wherein X is oxygen or a covalent bond, Q represents an alkylene group of formula —$(CH_2)_n$— where n is an integer from 1 to 6, in which one carbon atom other than a carbon atom bound to the oxygen atom or to X, when X is oxygen, is optionally substituted with hydroxyl, and $R_3$, $R_4$, $R_5$, $R_6$ and $R_7$ are each hydrogen, halogen, lower alkyl, lower alkoxy or lower alkanoyl, provided that at least one of $R_1$, $R_2$, $A_1$ or $A_2$ is hydrogen; see also Belgium Patent Nos. 846 385 and 854 639 for other examples.

European Patent Application No. 79301318.6 (U.S. Pat. No. 4,248,879) discloses that compounds of formula (B) can inhibit the release of these allergic response mediators:

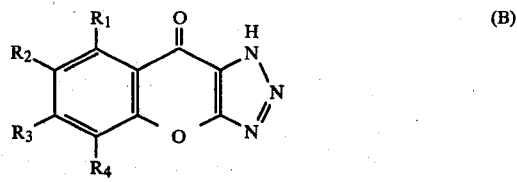

and pharmaceutically acceptable salts thereof, wherein $R_1$, $R_2$, $R_3$ and $R_4$, which may be the same or different, represent hydrogen, halogen, nitro, lower alkyl or lower alkoxy, or any adjacent two of $R_1$ to $R_4$ taken together represent an alkylene group containing from 3 to 5 carbon atoms or a 1,4-buta-1,3-dienylene group. These compounds do not have the ability to inhibit released SRS-A.

A novel class of compounds has now been discovered, which compounds have the ability to inhibit mediator release, and also to inhibit released SRS-A.

These novel compounds of the invention are thus of value in the prophylaxis and treatment of diseases whose symptoms are controlled by these mediators of the allergic response, for example asthma, hay fever, rhinitis and allergic eczema.

Accordingly, the present invention provides a compound of the formula (I), and pharmaceutically acceptable salts thereof:

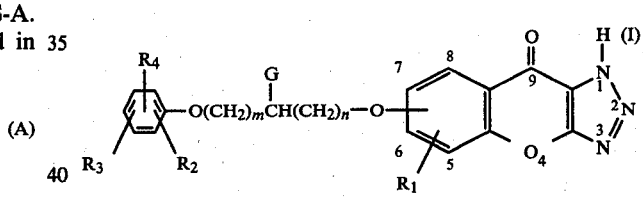

wherein
$R_1$ is hydrogen or $C_{1-6}$ alkyl;
$R_2$, $R_3$ and $R_4$ are the same or different and are chosen from hydrogen, hydroxyl, halogen, $C_{1-4}$ alkyl, $C_{1-4}$ alkoxy and $C_{1-4}$ alkanoyl;
G is H or OH; and
m and n are independently 1 to 3; with the proviso that when G is OH, one of m and n is 1.

It will be appreciated that the compounds of formula (I) may exist in a number of tautomeric forms, and it is to be understood that all such tautomeric forms are of course covered by the invention.

Suitable examples of $R_1$ include hydrogen, methyl, ethyl and n- and iso-propyl. When other than hydrogen, $R_1$ is suitably in the 5-position (that is, substituting the carbon atom adjacent to the oxygen atom joined bridgehead carbon atom). Preferably $R_1$ is hydrogen or 5-methyl or 5-n-propyl.

n may suitably be 1 or 2, preferably 1. More preferably m and n are each 1.

The phenoxyalkoxy side chain oxygen atom may join the benzopyrano[2,3-d]-v-triazole nucleus at any non-bridgehead carbon in the benzo moiety. More suitably however it will be joined at the 6-position (that is, substituting the carbon atom meta- to the bridgehead carbon atom linked to the ring-system oxygen atom).

Examples of $R_2$, $R_3$ and $R_4$ include hydrogen, and hydroxyl.

Examples of $R_2$ to $R_4$ when halogen include fluorine, chlorine and bromine, most suitably fluorine.

Examples of suitable $C_{1-4}$ alkyl substituents falling within the definitions of $R_2$ to $R_4$ are methyl, ethyl, n- and iso-propyl, n-, iso and t-butyl, preferably n-propyl.

Examples of suitable $C_{1-4}$ alkoxy substituents falling within the definitions of $R_2$ to $R_4$ are methoxy, ethoxy, n- and iso-propoxy.

Examples of suitable $C_{1-4}$ alkanoyl groups included within the definition of $R_2$ to $R_4$ are acetyl, propionyl, and n- and iso-butyryl, preferably acetyl.

Favourably only one of $R_2$ to $R_4$ is hydroxyl. When one of these groups is hydroxyl it is favourably in the 3-position in the phenyl ring with respect to the alkylenedioxy group.

Favourably only one of $R_2$ to $R_4$ is $C_{1-4}$ alkyl. When $C_{1-4}$ alkyl, such a group is favourably in the 2-position in the phenyl ring as hereinbefore defined.

Favourably only one of $R_2$ to $R_4$ is $C_{1-4}$ alkanoyl. When $C_{1-4}$ alkanoyl, such a group is favourably in the 4-position in the phenyl ring as hereinbefore defined.

Where a highly substituted compound of formula (I) is required it will be appreciated that the substituents are to be chosen for steric compatability. For example, where two or three of the substituents are groups such as highly branched $C_{1-4}$ alkyl, $C_{1-4}$ alkoxy or $C_{1-4}$ alkanoyl groups, then these will not occupy adjacent positions.

G is preferably OH.

The triazole moiety of the compounds has an acidic hydrogen, and accordingly may form salts. Examples of pharmaceutically acceptable salts falling within the scope of this invention include the aluminium, alkali metal and alkaline earth metal salts such as the sodium, potassium and magnesium salts; and salts with ammonia, organic bases and amino compounds.

From the aforesaid it will be appreciated that one sub-group of compounds of the formula (I) is of formula (II):

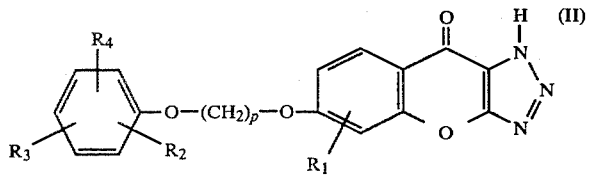

wherein p is 3 to 5; and the remaining variables are as defined in formula (I).

p is preferably 3.

Suitable and preferred variables $R_1$, $R_2$, $R_3$ and $R_4$ are as hereinbefore described, as are suitable and preferred substitution positions.

Thus when one of $R_2$, $R_3$ and $R_4$ is the only one of these variables to be $C_{1-4}$ alkyl it is preferably in the phenyl 2-position as hereinbefore defined. It is particularly preferably n-propyl.

When one of $R_2$, $R_3$ and $R_4$ is the only one of these variables to be hydroxy it is preferably in the phenyl 3-position as hereinbefore defined.

When one of $R_2$, $R_3$ and $R_4$ is the only one of these variables to be $C_{1-4}$ alkanoyl it is preferably in the phenyl group 4-position as hereinbefore defined.

A second group of compounds within those of the formula (I) is of the formula (III) and salts thereof:

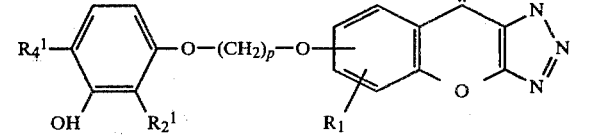

wherein:
$R_1$ is as defined in formula (I);
p is as defined in formula (II);
$R_2^I$ is $C_{1-4}$ alkyl; and
$R_4^I$ is $C_{1-4}$ alkanoyl.

Suitable and preferred values for $R_1$, p, $R_2^1$ and $R_4^1$ are as so described for $R_1$ and n and corresponding values of $R_2$ and $R_4$ respectively under formula (I), as are suitable and preferred substitution positions.

Thus $R_2^1$ is preferably n-propyl and $R_4^1$ is preferably acetyl; and often the side chain will substitute the benzo moiety at the 6-position.

One preferred group of compounds of the formula (I) is of formula (IV):

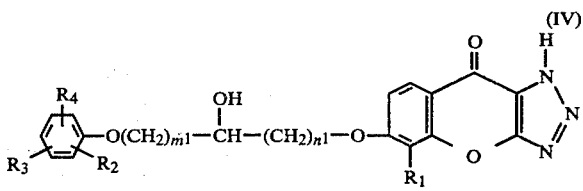

wherein
$m^1$ and $n^1$ are independently 1 or 2, and the remaining variables are as defined in formula (I).
$m^1$ and $n^1$ are preferably both 1.

Suitable and preferred variables $R_1$, $R_2$, $R_3$ and $R_4$ are as hereinbefore described under formula (II), as are suitable and preferred substitution positions.

A second preferred group of compounds within those of the formula (I) is of the formula (V) and salts thereof:

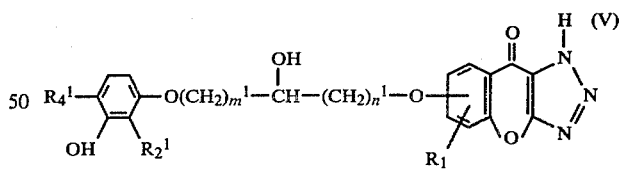

wherein
$R_1$, $m^1$ and $n^1$ are as defined in formula (IV)
$R_2^1$ is $C_{1-4}$ alkyl; and
$R_4^1$ is $C_{1-4}$ alkanoyl.

Suitable and preferred values for $R_1$, $m^1$, $n^1$, $R_2^1$ and $R_4^1$, and suitable and preferred substitution positions, are as described hereinbefore in relation to formulae (III) and (IV). Thus $R_2^1$ is preferably n-propyl and $R_4^1$ is preferably acetyl; often the side chain will substitute the benzo moiety at the 6-position; and $R_1$ will often be H, 5-methyl or 5-n-propyl.

(a) 6-[3-(4-Acetyl-3-hydroxy-2-n-propylphenoxy)-propan-1-yloxy]-5-methyl-9-oxo-1H,9H-benzopyrano[2,3-d]-v-triazole, (b) 6-[3-(4-Acetyl-3-hydroxy-2-n-propylphenoxy)-2-hydroxypropan-1-yloxy)-5-methyl-9-oxo-1H,9H-benzopyrano[2,3-d]-v-triazole, (c) 6-[3-(4-Acetyl-3-hydroxy-2-n-propylphenoxy)-2-hydroxypropan-1-yloxy]-9-oxo-5-n-propyl-1H,9H-benzopyrano[2,3-d]-v-triazole, (d) 6-[3-(4-Acetyl-3-hydroxy-2-n-propylphenoxy)-2-hydroxypropan-1-yloxy]-9-oxo-1H,9H-benzopyrano[2,3-d]-v-triazole, (e) 7-[3-(4-Acetyl-2-hydroxy-2-n-propylphenoxy)-2-hydroxypropan-1-yloxy]-9-oxo-1H,9H-benzopyrano[2,3-d]-v-triazole, (f) 6-[3-(4-Acetyl-3-hydroxy-2-n-propylphenoxy)propan-1-yloxy]-5-n-propyl-9-oxo-1H,9H-benzopyrano[2,3-d]-v-triazole, (g) 6-[3-(4-Acetyl-3-hydroxy-2-n-propylphenoxy)-propan-1-yloxy]-9-oxo-1H,9H-benzopyrano[2,3-d]-v-triazole, (h) 7-[3-(4-Acetyl-3-hydroxy-2-n-propylphenoxy)-propan-1-yloxy]-9-oxo-1H,9H-benzopyrano[2,3-d]-v-triazole, are typical compounds of the present invention.

The present invention also provides a process for the preparation of a compound of the formula (I), which process comprises the de-protection of a compound of the formula (VI):

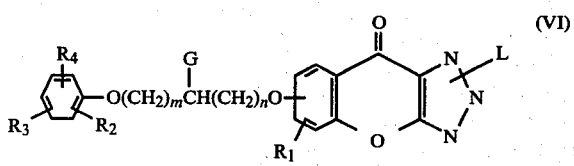

wherein L is a protecting group and the remaining variables are as defined in formula (I).

L may suitably be an N-protecting group removable by acidolysis with a strong acid. Suitable examples of L include labile benzyl groups or trityl. Examples of labile benzyl groups include benzyl substituted in the phenyl ring by one or more $C_{1-4}$ alkoxy groups, such as 4-methoxy, 2,4-dimethoxy or 2,4,6-trimethoxy-benzyl. A particularly suitable example of L is 4-methoxybenzyl.

L may be removed in any convenient way which does not disrupt any other part of the molecule, such as by acidolysis. Strong acids such as trifluoroacetic or methanesulphonic acids are suitable. The reaction may of course be monitored by n.m.r. spectroscopy or high pressure liquid chromatography, but we have found that a temperature of 50° to 70° C. and a reaction time of 2 to 9 hours are appropriate.

The compounds of the formula (VI) may themselves be prepared by coupling a compound of the formula (VII):

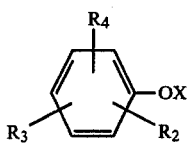

with a compound of the formula (VIII):

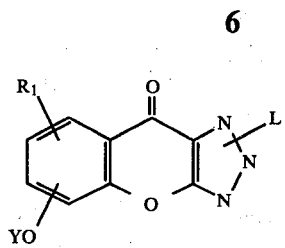

wherein X is hydrogen and Y is a group $Z(CH_2)_mCH_2(CH_2)_n$ where Z is hydroxyl or a group readily displaceable by a nucleophile from an aliphatic moiety, or Y is hydrogen and X is a group $(CH_2)_mCH_2(CH_2)_nZ$ where Z is as defined, the remaining variables being as defined in formula (I); to give a compound of the formula (VI) wherein G is hydrogen; or wherein X is

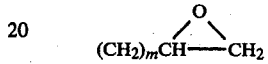

or $(CH_2)_m$ CH(OH)CH$_2$Cl and Y is hydrogen or Y is

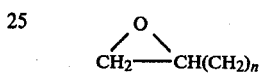

or CH$_2$ClCH(OH) (CH$_2$)$_n$ and X is hydrogen, to give a compound of formula (VI) wherein G is hydroxyl and n or m respectively is 1.

When Z is a group readily displaceable by a nucleophile, suitable examples of Z include halogen atoms such as chlorine, bromine and iodine, and activated ester groups such as methanesulphonate and tosylate groups.

When one of $R_2$ to $R_4$ is hydroxyl it will in general be necessary to protect such a hydroxyl group during the above reaction. This may suitably be effected by conversion to a benzyloxy group, optionally monosubstituted by methoxy or nitro before reaction, the benzyloxy group being converted to hydroxy by conventional hydrogenolysis after the reaction. If such a hydroxy group is adjacent to another one of $R_2$ to $R_4$ which is $C_{1-4}$ alkanoyl, protection is not necessary.

When in the compounds of the formula (VII) and (VIII), X is a group $(CH_2)_nCH_2(CH_2)_nZ^1$ or Y is a group $Z^1(CH_2)_mCH_2(CH_2)_n$, where $Z^1$ is a group readily displaced by a nucleophile from an aliphatic moiety and when Y or X respectively will be hydrogen, the reaction is generally carried out in the presence of a moderate base in a polar solvent. Examples of suitable bases include basic alkali metal salts such as the carbonates, for instance potassium carbonate. Examples of suitable solvents include ketones; such as methyl ethyl ketone.

The reaction is conveniently carried out under reflux at temperatures of 50° to 110° C. depending on the solvent, base and particular starting materials employed. The reaction time will depend on these parameters and on the temperature employed and this may readily be determined by routine trial and error. The reaction may be monitored by conventional methods such as thin layer chromatography. By way of example a reaction time of up to 6 hours is often suitable.

When in the compounds of the formulae (VII) and (VIII), X is a group $(CH_2)_mCH_2(CH_2)_nOH$ or Y is a group $HO(CH_2)_mCH_2(CH_2)_n$, when Y and X respectively will be hydrogen, the reaction of these compounds is generally carried out in the presence of a compound of formula (IX):

R₃O₂C—N=N—CO₂R₄ (IX)

wherein R₃ and R₄ are independently C₁₋₆ alkyl, aryl or aryl-C₁₋₆ alkyl, generally both ethyl, and a compound of formula (X):

PR₅R₆R₇ (X)

wherein R₅, R₆ and R₇ are independently C₁₋₆ alkyl, C₁₋₆ alkoxy, aryl, aryloxy, aryl-C₁₋₆ alkyl or aryl-C₁₋₆ alkoxy, generally all phenyl.

The reaction is generally carried out at a nonextreme temperature, such as −20° to 100° C., in an inert aprotic organic solvent such as tetrahydrofuran, dioxan, ethyl acetate or benzene.

When in the compounds of the formula (VII) and (VIII), X is a group

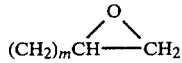

or (CH₂)ₘCH(OH)CH₂Cl or Y is a group

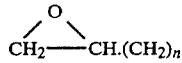

or CH₂ClCH(OH) (CH₂)ₙ, when Y or X respectively will be hydrogen, the reaction is generally carried out in the presence of a phase transfer catalyst such as benzyltrimethylammonium hydroxide, conveniently at temperatures of 50° to 110° C., in a polar solvent such as dimethylformamide. A temperature dependent reaction time of 4 to 14 hours is usually sufficient.

Compounds of the formula (VII) wherein X is hydrogen are either known compounds or prepared analogously to known compounds.

Compounds of the formula (VII) wherein X is (CH₂)ₘCH₂(CH₂)ₙZ as defined or

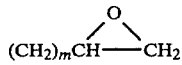

or (CH₂)ₘCH(OH)CH₂Cl may be prepared by reacting the corresponding compound of the formula (VII) wherein X is H with a compound of the formula (XIA), (XIB) or (XIC) respectively:

B(CH₂)ₘCH₂(CH₂)ₙZ (XIA)

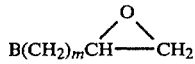

B(CH₂)ₘCH(OH)CH₂Cl (XIC)

wherein B is chlorine, bromine or iodine. Z when hydroxy may be subsequently conventionally esterified to give an activated ester group.

Compounds of the formula (VIII) wherein Y is Z(CH₂)ₘCH₂(CH₂)ₙ as defined or

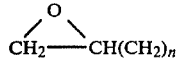

or CH₂ClCH(OH)(CH₂)ₙ may similarly be prepared by reacting the corresponding compound of the formula (VIII) wherein Y is H with a compound of the formulae (XID), (XIE) or (XIF) respectively:

Z(CH₂)ₘCH₂(CH₂)ₙB (XID)

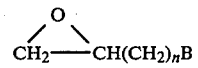 (XIE)

CH₂ClCH(OH)(CH₂)ₙB (XIF)

wherein B is as hereinbefore defined. Z may be esterified subsequently as indicated above.

The reaction is generally carried out in the presence of a strong base in a polar solvent, some of the polar solvent often serving to form the base. Examples of suitable bases include potassium carbonate in a ketonic solvent, or DMF, sodium in an alcohol such as tert-butanol, sodium hydride or hydroxide in dimethylsulphoxide or dimethylformamide and lithium di-isopropylamide in hexamethylphosphoramide. Temperatures of 5° to 90° C. may be used depending on the solvent, base and particular starting materials employed. The reaction time will depend on these parameters and on the temperature employed and this may readily be determined by routine trial and error. The reaction may be monitored by conventional methods such as thin layer chromatography. A temperature dependent reaction time of 4–14 hours is usually sufficient.

Compounds of the formula (VIII) wherein Y is H may be prepared by reaction of a compound of formula (XII):

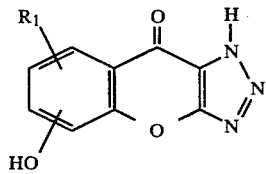 (XII)

with a compound of formula LB wherein L and B are as hereinbefore defined.

The reaction may suitably be effected using a base such as an alkali metal carbonate, suitably potassium, in a polar aprotic solvent such as dimethyl formamide at temperatures between 20° and 120°, suitably around 40°–50° C.

In a preferred synthetic route compounds of the formula (XII) may be prepared by dealkylation of an ether of the formula (XIII):

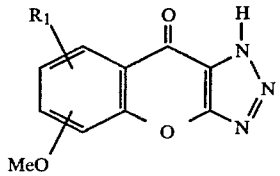 (XIII)

This may suitably be effected with a base such as sodium thioethoxide in a polar solvent such as dimethylformamide, at moderately elevated temperatures such as 130° to 170° C., following the procedure of Feutrill et al., Tet. Letters, 1970, 1327. Reflux for 1-2 hrs in dimethylformamide is usually sufficient for reaction.

Alternatively for the preparation of compounds of the formula (VIII), a compound of formula (XIV):

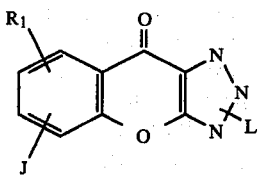
(XIV)

wherein J is an activated ester group, for example $C_{1-4}$ alkylsulphonyloxy, such as methylsulphonyloxy, or p-toluenesulphonyloxy may be hydrolysed to give a compound of formula (VIII) where Y is H.

This hydrolysis is suitably carried out under alkaline conditions.

The compounds of formula (XIV) may themselves be prepared by protecting the corresponding compound of formula (XV):

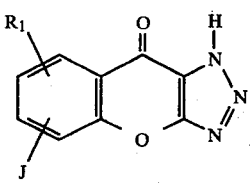
(XV)

by reaction with a compound LB as hereinbefore defined under the conditions hereinbefore described.

It will be appreciated of course that hydrolysis of a compound of the formula (XV) will yield a compound of formula (XII) as defined, thus providing a second route to compounds of the formula (VIII).

Compounds of the formulae (XII) and (XV), that is the respective precursors for the two synthetic routes to compounds of the formula (VIII), may be prepared by cyclisation of a compound of the formula (XVI):

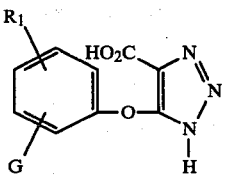
(XVI)

wherein G is J as hereinbefore defined, when a compound of formula (XV) is formed, or MeO when a compound of formula (XIII) is formed.

The cyclisation is preferably carried out at elevated temperature i.e. above 40° C. but less than 120° C. We have found temperatures between 80° and 105° C. to be convenient.

Compounds of formula (XVI) where G is J may be prepared by sulphonation of the corresponding compound of formula (XVII):

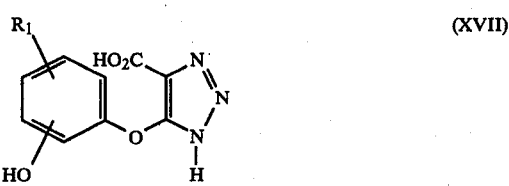
(XVII)

Sulphonation is carried out in conventional manner.

It should be noted that when mesylation is desired, this may suitably be carried out with a solution of phosphoric oxide in anhydrous methane-sulphonic acid, and if the reaction temperature is held at about 95° C. this mesylate gradually cyclises to the corresponding compound of formula (XV) as defined above.

The compound of formula (XVI) wherein G is J may alternatively be prepared by sulphonation of an ester of formula (XVIII):

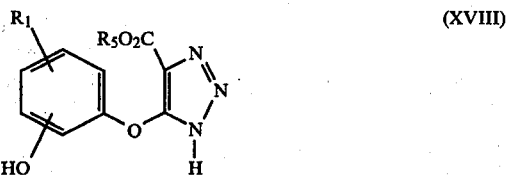
(XVIII)

wherein $R_5$ is $C_{1-6}$ alkyl, such as ethyl; or benzyl; and subsequent de-esterification.

The compound of formula (XVIII) is suitably prepared by hydrogenation of a compound of formula (XVIIIA):

(XVIIIA)

Q' and Q" are conventionally hydrogenolysable benzyl group, such as benzyl, 4-nitrobenzyl or 4-methoxybenzyl to give a compound of formula (XVIII) as defined above.

Subsequent de-esterification (with for example sodium hydroxide) of course gives a compound of formula (XVII) as defined above.

The aforesaid hydrogenation is conveniently carried out under conditions which remove both the benzyl protecting groups, for example with a palladium catalyst at about 1000 psi and 70°-100° C. However a stepwise hydrogenation is possible, as the O-benzyl group can be removed selectively under mild conditions.

When Q" is 4-methoxybenzyl these groups can be conveniently removed using trifluoroacetic acid at temperatures between 40° and 80° C., suitably 60°.

The compounds of formulae (XVI) (G=MeO) or (XVIII)A may themselves be prepared by reacting a phenol of formula (XIX):

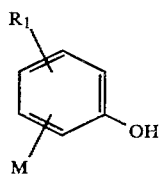

where M is MeO or Q′O, as its sodium salt, with an ester of formula (XX):

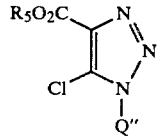

N-Deprotection and hydrolysis then gives (XVI) (G=MeO).

The salts of the compounds of the formula (I) may be prepared in the usual manner from the corresponding 'free' compounds of the formula (I).

As previously indicated, the compounds of formula (I) have the ability to inhibit the release of the mediators of the allergic response, and also to inhibit released SRS-A, and thus may be used therapeutically in the treatment of allergy.

The level of the compounds's activity against released SRS-A is particularly interesting.

Some of the compounds of the formula (I) mainly those wherein G is H, show indications of a usefully enhanced duration of action.

This invention also provide a pharmaceutical composition comprising a compound of formula (I) as defined above, or a pharmaceutically acceptable salt thereof, and a pharmaceutically acceptable carrier.

Examples of suitable and preferred compounds for inclusion in such compositions are as previously discussed.

The compositions are of course adapted for administration to human beings.

Compounds of formula (I) which are active when given by the oral route, may be compounded in the form of syrups, tablets, capsules, pills and the like. Preferably, the compositions are in unit dosage form, or in a form in which the patient can administer to himself a single dosage. When the composition is in the form of a tablet, powder or lozenge, any pharmaceutical carrier suitable for formulating solid compositions may be used. Examples of such carriers are magnesium stearate, starch, lactose, glucose, sucrose, rice flour and chalk. The composition may also be in the form of an ingestible capsule (e.g. of gelatin) containing the compound; or in the form of a syrup, a liquid solution or a suspension. Suitable liquid pharmaceutical carriers include ethyl alcohol, glycerine, saline and water which may be compounded with flavouring or colouring agents to form syrups.

The compounds of this invention may also be administered by a non-oral route. In accordance with routine pharmaceutical procedure, the compositions may be formulated, for example for rectal administration as a suppository or for presentation in an injectable form in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, anti-oxidants or other preservatives, buffers, solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appripriate dose may be withdrawn or a solid form or concentrate which can be used to prepare an injectable formulation.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns. Where appropriate, small amounts of other anti-asthmatics and bronchodilators for example sympathomimetic amines such as isoprenaline, isoetharine, salbutamol, phenylephrine and ephedrine; xanthine derivatives such as theophylline and aminophylline and corticosteroids such as prednisolone and arenal stimulants such as ACTH may be included.

Compounds of general formula (I) may also be presented as an ointment, cream, lotion, gel, aerosol, or skin paint for topical application.

It is preferred that the compounds of this invention are administered by inhalation.

By way of example, in any of the preceding formulations a suitable dosage unit might contain 0.01 to 500 mgs of active ingredient, more suitably 1 to 500 mgs via the oral route, 0.01 to 1 mgs via inhalation. The effective dose of compound (I) depends on the particular compound employed, the condition of the patient and on the frequency and route of administration, but in general is in the range of from 0.001 mg/kg/day to 100 mg/kg inclusive of the patient's body weight.

As in common practice, the compositions will usually be accompanied by written or printed directions for use in the medical treatment concerned, in this case as an anti-allergic agent for the prophylaxis and treatment of for example, asthma, hay fever, rhinitis or allergic eczaema.

The following Examples illustrate the preparation of compounds of this invention.

The following Descriptions illustrate the preparation of intermediates to these compounds.

DESCRIPTION 1

(a) 3-Benzyloxy-2-methylphenol

Anhydrous potassium carbonate (30.4 g) was added to a stirred solution of 2-methylresorcinol (24.8 g) in N,N-dimethylformamide (DMF, 250 ml) and benzyl chloride (25.3 g) was added over 15 minutes. The mixture was heated to 80° C. and maintained at this temperature overnight with continued stirring. On cooling the DMF was removed in vacuo to give an oil which was partitioned between water and ether. The dried ethereal phase was evaporated and chromatographed on silica eluting with chloroform to give 9.78 g (23%) of the title compound of mp 58°-59° C. (Found: C, 78.16; H, 6.63; $C_{14}H_{14}O_2$ requires C, 78.48; H, 6.58%).

(b) Ethyl 1-benzyl-5-(3-benzyloxy-2-methylphenoxy)-v-triazole-4-carboxylate

A 50% dispersion of sodium hydride in mineral oil (1.68 g, 0.035 mole) was added to a stirred solution of 3-benzyloxy-2-methylphenol (7.5 g, 0.035 mole) in dry DMF (200 ml) and to the resulting sodium salt was added a solution of ethyl 1-benzyl-5-chloro-v-triazole-4-carboxylate (9.30 g, 0.035 mole) in dry DMF (20 ml). The reaction mixture was heated with stirring at 80° C. for 24 hours and then cooled. Removal of the DMF in vacuo gave a dark oil which was taken up in chloroform, washed with water and dried. Evaporation gave an oil which crystallised on standing. Recrystallisation (from ethanol) gave 10.27 g (66%) of product of mp 98°–99° C. (Found: C, 70.48; H, 5.76; N, 9.54; $C_{26}H_{25}N_3O_4$ requires C, 70.41; H, 5.68; N, 9.48%).

(c) Ethyl 5-(3-hydroxy-2-methylphenoxy)1H-v-triazole-4-carboxylate

Hydrogenolysis of a solution of ethyl 1-benzyl-5-(3-benzyloxy-2-methylphenoxy)-v-triazole-4-carboxylate (10 g) in ethanol (300 ml) over 10% palladium on charcoal at 100° C. and 1000 psi resulted in a clean removal of both the O- and N-benzyl groups within 3 hours. On cooling and removal of the catalyst by filtration, evaporation of the solvent gave an oil which after filtration through a kieselgel column in chloroform gave 4.20 g (71%) of product of mp 120°–122° C. (Found: C, 54.62; H, 5.04; N, 16.19; $C_{12}H_{13}N_3O_4$ requires C, 54.75; H, 4.98; N, 15.96%).

(d) 5-(3-Hydroxy-2-methylphenoxy)-1H-v-triazole-4-carboxylic acid

Hydrolysis of ethyl 5-(3-hydroxy-2-methylphenoxy)-1H-v-triazole-4--carboxylate (2 g) with 5% aqueous sodium hydroxide (30 ml) at 80° C. over 1 hour afforded the acid which was isolated by acidification of the cooled (0° C.) solution. Recrystallisation from aqueous ethanol gave 1.47 g (82%) of material of mp 141°–143° C. (Found: C, 50.71; H, 3.85; N, 17.70; $C_{10}H_9N_3O_4$ requires: C, 51.06; H, 3.86; N, 17.87%)

(e) 6-Mesyloxy-5-methyl-9-oxo-1H,9H-benzopyrano[2,3-d]-v-triazole (i) To a solution of phosphoric oxide (21 g) in 98% methane sulphonic acid (90 g) at 60° C. was added 5-(3-hydroxy-2-methylphenoxy)-1H-v-triazole-4-carboxylic acid (2.8 g) with stirring and the mixture maintained at 100° C. After 22 hours at this temperature hplc monitoring showed the absence of starting material. The mixture was cooled, diluted with ice water and the product extracted into ethyl acetate. Evaporation of the dried extracts gave an oily solid which was recrystallised from ethanol in the presence of charcoal to give 1.39 g (40%) of the title compound of mp 183°–190° C. Further recrystallisation gave material of mp 211°–212° C., δ (DMSO) 2.50 (3H, s); 3.58 (3H, s); 4.6 (broad exchangeable); 7.88 (2H, AB quartet J 9.0 Hz; Δν57 Hz); M+ 295.0265 ($C_{11}H_9N_3SO_5$) (Found: C, 44.65; H, 2.65; N, 13.75; $C_{11}H_9N_3SO_5$ requires C, 44.4; H, 3.05; N, 14.2%); (second analysis: Found: C, 44.78; H, 2.89; N, 13.96%).

(ii) A similar treatment of 5-(3-mesyloxy-2-methylphenoxy)-1H-v-triazole-4-carboxylic acid (0.1 g, mp 144° C., prepared from the hydroxy compound with $P_2O_5$ in methane sulphonic acid at 70° C.) gave, after recrystallisation from ethanol, 0.07 g (74%) of cyclic product of mp 205°–207° C. and identical with that prepared above.

(f) 6-Mesyloxy-N-(4-methoxybenzyl)-5-methyl-9-oxo-9H-benzopyrano[2,3-d]-v-triazoles The above mesylate (7.00 g; 0.024 mole) was dissolved in anhydrous DMF (150 ml) and treated with anhydrous potassium carbonate (5.00 g; 0.036 mole) and 4-methoxybenzyl chloride (4.5 g, small excess). The mixture was stirred at room temperature for 72 hours after which time the solvent was removed in vacuo. Water and ethyl acetate were added to the residue and the phases separated. After evaporation of the dried organic phase the resulting oil was chromatographed to give (6.32 g, 63%) of a 1:1 mixture of mixed isomers believed to be the N-1 and N-2 derivatives. Rechromatography of a small sample of this mixture afforded pure samples of the individual isomers.

N-1 isomer: mp (EtOH/CHCl₃)) 149°–153° C., $v_{max}$ (mull) 1678, 1603, 1520, 1512, 1363 cm$^{-1}$; δ (CDCl₃) 2.55 (3H, s), 3.27 (3H, s); 3.72 (3H, s); 5.88 (2H, s); 6.81 (2H, d, J 9 Hz); 7.38 (1H, d, J 9 Hz); 7.45 (2H, d, J 9 Hz); 8.20 (1H, d, J 9 Hz); M+ 415.0809 ($C_{19}H_{17}N_3O_6S$). (Found: C, 54.7; H, 4.3; N, 9.9; S, 7.55; $C_{19}H_{17}N_3O_6S$ requires: C, 54.95; H, 4.1; N, 10.1; S, 7.7%)

N-2 isomer: mp (EtOH) 170°–172° C., $v_{max}$ (mull) 1680, 1612, 1545, 1520 cm$^{-1}$, δ (CDCl₃) 2.50 (3H, s); 3.30 (3H, s); 3.77 (3H, s); 5.62 (2H, s); 7.15 (4H, AB quartet, Δν45 Hz, J 10 Hz); 7.42 (1H, d, J 10 Hz); 8.28 (1H, d, J 9 Hz). M+ 415.0837 ($C_{19}H_{17}N_3O_6S$). (Found; C, 54.7; H, 4.35; N, 10.1; S, 7.5; $C_{19}H_{17}N_3O_6S$ requires: C, 54.95; H, 4.1; N, 10.1; S, 7.7%).

(g) 6-Hydroxy-N-(4-methoxybenzyl)-5-methyl-9-oxo-9H-benzopyrano[2,3-d]-v-triazoles The mixture of 4-methoxybenzyl triazoles (0.7 g) was treated with 1.25 M sodium hydroxide (70 ml) and ethanol (20 ml) added. After stirring at 80° C. for 5 hours the hydrolysis was complete by tlc and the reaction mixture was cooled and acidified at 0° C. The white solid which separated was filtered off, washed well with water and dried in vacuo over $P_2O_5$ to give 0.595 g (100%) of material of mp 219°–226° C. Recrystallisation from ethanol gave mixed isomers of mp 229°–239° C. (Found: C, 63.70; H, 4.12; N, 12.19; $C_{18}H_{15}N_3O_4$ requires: C, 64.09; H, 4.48; N, 12.46%).

Pure N-1 isomer and pure N-2 isomer were readily obtained by hydrolysis of the individual mesylate isomers as described above for the mixture.

(i) 6-Hydroxy-1(4-methoxybenzyl)-5-methyl-9-oxo-9H-benzopyrano[2,3-d]-v-triazole

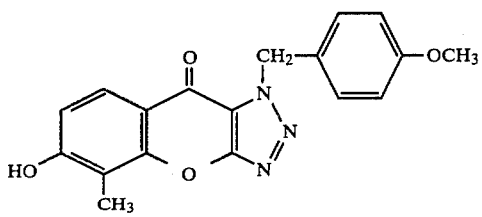

Hydrolysis of 6-methanesulphonyloxy-1-(4-methoxybenzyl)-5-methyl-9-oxo-9H-benzopyrano[2,3-d]-v-triazole (1.494 g) with 5% aqueous sodium hydroxide, (153 ml), and ethanol, (40 ml), at 80° C. for 3 hours afforded the hyroxy compound, which was isolated by acidification of the cooled, yellow solution. Recrystallization from ethanol gave 0.592 g (49%) of white material.

mp 257°-8° C. (dec)

$\nu$max (mull) 1615, 1660, 3120 cm$^{-1}$ $\delta$, DMSOd$_6$; 2.30, (3H, s), 3.75 (3H, s), 5.89 (2H, s), 7.03 (1H, d, J 9 Hz), 7.13 (4H, ABq, $\Delta\nu$42 Hz, J 9 Hz), 7.92 (1H, d, J 9 Hz), 11.0 (1H, broad, exchanges with D$_2$O)

Found C, 64.17, H, 4.72 N, 12.46, C$_{18}$H$_{15}$N$_3$O$_4$ requires C, 64.09; H, 4.48, N, 12.46%

(ii) 6-Hydroxy-2-(4-methoxybenzyl)-5-methyl-9-oxo-9H-benzopyrano[2,3-d]-v-triazole

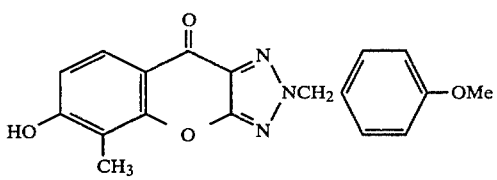

Hydrolysis of 6-methanesulphonyloxy-2-(4-methoxybenzyl)-5-methyl-9-oxo-9H-benzopyrano[2,3-d]-v-triazole (1.22 g) with 5% aqueous sodium hydroxide, (125 ml), and ethanol, (35 ml), at 80° C. for 3 hours afforded the hydroxy compound, which was isolated by acidification of the cooled yellow solution. Recrystallization from ethanol gave 0.477 g, (47%), of white material.

mp 264°-5° C., (dec), $\nu$max (mull), 1605, 1670, 3215 cm$^{-1}$ $\delta$,DMSOd$_6$: 2.25 (3H, s), 3.74 (3H, s), 5.70 (2H, s), 6.94 (1H, d, J 9 Hz), 7.13 (4H, ABq, $\Delta\nu$40 Hz, J 9 Hz), 7.88 (1H, d, J 9 Hz), 10.90 (1H, s, exchanges with D$_2$O).

Found C, 64.06; H, 4.68; N, 12.44; C$_{18}$H$_{15}$N$_3$O$_4$ requires C, 64.09; H, 4.48; N, 12.46%).

M$^+$=337.1063 (C$_{18}$H$_{15}$N$_3$O$_4$)

(h) 6-[3-(4-Acetyl-3-hydroxy-2-n-propylphenoxy)propan-1-yloxy]-N-(4-methoxybenzyl)-5-methyl-9-oxo-9H-benzopyrano[2,3-d]-v-triazole A solution of the mixed isomers of 6-hydroxy N-(4-methoxybenzyl)-5-methyl-9-oxo-9H-benzopyrano[2,3-d]-v-triazole (202 mg, 0.6 mmole), 3-(4-acetyl-3-hydroxy-2-n-propylphenoxy) propan-1-ol, (152 mg, 0.6 mmole), and triphenylphosphine, (441 mg, 1.68 mmole), in dry tetrahydrofuran, (20 ml) was magnetically stirred at 20° C. and diethylazodicarboxylate, (293 mg, 1.63 mmole) dissolved in dry THF (1 ml) added dropwise. After stirring at 20° C. for 2.5 hours, the reaction was complete by HPLC. The solvent was evaporated in vacuo and the yellow residue boiled in ethanol. On cooling the white solid which crystallised out was collected by filtration and dried in vacuo over CaCl$_2$ to give 233 mg (73%) of mixed isomers, of mp. 135°-171° C.

Pure N-2 isomer could be obtained by fractional crystallisation from ethanol or column chromatography using SiO$_2$ eluting with CHCl$_3$/petrol 60°-80° C. [1:1]→CHCl$_3$.

Physical Data N-2 isomer mp. (EtOH) 170°-1° C., $\nu$max (mull) 1680, 1635, 1615 cm$^{-1}$, $\delta$(CDCl$_3$) 0.98 (3H, t, J 7 Hz), 1.50 (2H,m), 1.52 (3H,s), 2.50 (4H,m), 2.56 (3H,s), 3.79 (3H, s), 4.31 (4H,2t,J 6 Hz), 5.62 (2H,s), 6.46 (1H,d,J 9 Hz),6.99 (1H,d, obscured), 7.15 (4H,ABq, $\Delta\nu$34 & 9 Hz), 7.59 (1H,d, J 9 Hz), 8.24 (1H,d, J 9 Hz), 12.71 (1H,s) (Found; C 66.87, H 6.07, N 7.22.

C$_{32}$H$_{33}$N$_3$O$_7$ requires C 66.53, H 5.94, N 7.51)

M$^+$=571.2351 (C$_{32}$H$_{33}$N$_3$O$_7$)

EXAMPLE 1

6-[3-(4-Acetyl-3-hydroxy-2-n-propylphenoxy)propan-1-yloxy]-5-methyl-9-oxo-1H,9H-benzopyrano[2,3,d]-v-triazole

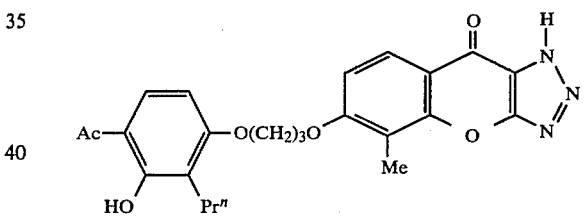

A solution of the above isomeric mixture (190 mg, 0.34 mmole) in trifluoroacetic acid (5 ml) was heated with magnetic stirring at 65° C. (oil bath temperature). After 3.5 hours HPLC showed a trace of starting material left. The reaction was cooled and evaporated in vacuo to dryness. The blue residue was chromatographed on silica, eluting with CHCl$_3$/10% methanol, to give 114 mg of crude title compound. Recrystallisation from N,N-dimethylformamide gave 44 mg (29%) of pure product containing 1 molecule of solvent.

m.p. (DMF) 155°-6° C.

$\delta$(DMSO d$_6$) 0.84 (3H,t,J 7 Hz), 1.40 (4H,m), 2.08 (2H,m), 2.36 (3H,s), ca 2.5 (3H,s), 4.36 (4H,dt, J 7 Hz), 6.68 (1H,d,J 9 Hz), 7.24 (1H,d,J 9 Hz), 7.82 (1H,d,J 9 Hz), 8.12 (1H,d,J 9 Hz), 12.80 (1H,s). (Found C 61.51, H 6.22, N 10.66 C$_{24}$H$_{25}$N$_3$O$_6$.C$_3$H$_7$NO; requires C 61.82, H 6.15, N 10.68.

M$^+$=451.1710, (C$_{24}$H$_{25}$N$_3$O$_6$).

Recrystallization from methanol/CHCl$_3$ gave the title compound mp 223°-5° C. (dec) $\nu$(max) mull, 1605 (shoulder at 1610) 1680 cm$^{-1}$.

(Found C 63.61, H 5.40, N 9.01, C$_{24}$H$_{25}$N$_3$O$_6$ requires C 63.85, H 5.58, N 9.31%).

6-[3-(4-Acetyl-3-hydroxy-2-n-propylphenoxy)-propan-1-yloxy]-5-methyl-9-oxo-1H,9H-benzopyrano-[2,3-d]-v-triazole, mono sodium salt A stirred solution of 1 M aqueous sodium hydroxide (1.0 ml) was added dropwise to a warm solution of the above compound (0.50 g) in DMF (50 ml) to give a solution of pH 7.5. The solvent was evaporated in vacuo and the white residue recrystallised from ethanol to yield 0.52 g (99%) of sodium salt.

$\nu_{max}$ (mull): 1618, 1638, shoulder at 1665, 3350 (broad)cm$^{-1}$ $\delta$DMSO-d$_6$: 0.80 (3H, t, J 6 Hz); 1.38 (2H, m); 2.32 (3H, s); 2.32 (2H, m); 2.60 (3H, s); 4.30 (4H, 2t, J 6 Hz); 6.67 (1H, d, J 9 Hz); 7.07 (1H, d, J 9 Hz); 12.86 (1H, s, exchanged D$_2$O).

Found: C, 59.99; H, 5.46; N, 8.41; (C$_{24}$H$_{24}$NaN$_3$O$_6$0.5H$_2$O requires: C, 59.74; H, 5.22; N, 8.71%).

DESCRIPTION 2

6-[3-(4-Acetyl-3-hydroxy-2-n-propylphenoxy)-2-hydroxypropan-1-yloxy]-1-(4-methoxybenzyl)-5-methyl-9-oxo-9H-benzopyrano[2,3-d]-v-triazole A solution of pure 6-hydroxy-1-(4-methoxybenzyl)-5-methyl-9-oxo-9H-benzopyrano[2,3-d]-v-triazole (300 mg, 0.89 mmole), and 4-(2,3-epoxypropoxy)-2-hydroxy-3-n-propylacetophenone, (245 mg, 0.97 mmole), in dry dimethylformamide, (20 ml), was treated with Triton B., [a 40% solution of N-benzyltrimethylammonium hydroxide in methanol] (10 drops) and the orange solution stirred at 140° C. for 5 hours, after which time TLC showed the reaction was complete. On cooling, the solvent was evaporated in vacuo and the red residue partitioned between ethyl acetate and water. The organic phase was separated, washed with brine, dried, (MgSO$_4$), and evaporated in vacuo. The red residue was chromatographed on silica, eluting with CH$_2$Cl$_2$ to CHCl$_3$ to give a colourless oil, which on boiling with ethanol and cooling gave a white fluffy solid which was collected by filtration and dried in vacuo to yield 186 mg (32%) of the title compound of mp 154°-5° C., $\nu$max (mull) 1605, 1665 cm$^{-1}$, $\delta$, (CDCl$_3$) 0.92 (3H, t, J 7.5 Hz), 1.54 (2H, m), 2.60 (2H, m), 2.57 (3H, s), 3.77 (3H, s), 4.31 (5H, m), 5.91 (2H, s), 6.48 (1H, d, J 9 Hz), 6.85 (1H, obscured), 7.04 (1H, d, J 9 Hz), 7.12 (4H, ABq, $\Delta\nu$=52 Hz, J 9 Hz), 7.61 (1H, d, J 9 Hz), 8.20 (1H, d, J 9 Hz), 12.73 (1H, s)

Found; C, 64.97; H, 5.69; N, 7.08; C$_{32}$H$_{33}$N$_3$O$_8$ requires C, 65.41; H, 5.60; N, 7.15%

EXAMPLE 2

6-[3-(4-Acetyl-3-hydroxy-2-n-propylphenoxy)-2-hydroxypropan-1-yloxy]-5-methyl-9-oxo-1H,9H-benzopyrano[2,3-d]-v-triazole

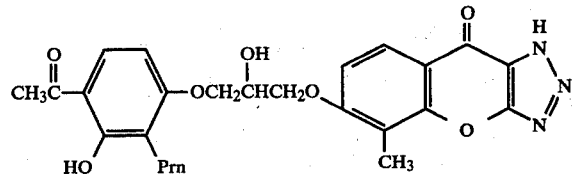

A solution of the above compound, (200 mg, 0.34 mmole), in trifluoroacetic acid, (5 ml), was heated with stirring, at 65° C., (oil bath temperature). After 5 hours HPLC showed no starting material left. The reaction was cooled and evaporated in vacuo to dryness. The residue was chromatographed on silica eluting with CHCl$_3$ to CHCl$_3$/5% methanol to give 28 mg (18%), of product, mp (EtOH/H$_2$O) 120° C., $\nu$max (mull), 1605, 1675 (weak) cm$^{-1}$.

$\delta$((CD$_3$)$_2$SO) 0.79 (3H, t, J 7 Hz), 1.41 (2H, m), 1.89 (2H, m), 2.34 (3H, s), 3.27 (3H, s), 4.29 (5H, m), 5.50 (1H, broad s, exchanged D$_2$O), 6.70 (1H, d, J 9 Hz), 7.26 (1H, d, J 9 Hz), 7.81 (1H, d, J 9 Hz), 8.10 (1H, d, J 9 Hz), 12.80 (1H, s, exchanged D$_2$O).

Found C; 58.89, H; 5.90 N; 8.26; C$_{24}$H$_{25}$N$_3$O$_7$.H$_2$O. requires C; 59.37, H; 5.60, N 8.66%). M$^+$=467.1630 (C$_{24}$H$_{25}$N$_3$O$_7$).

Other material was collected with a peak at 1795 cm$^{-1}$ in the infrared spectrum, which suggests a trifluoroacetate of the glycerol side chain. Alkaline hydrolysis of this yields the free hydroxy compound.

In a second reaction the title compound was prepared in 53% yield using a hydrolytic work-up, mp 135°-7° C., $\nu_{max}$ (mull): 1610, 1675 cm$^{-1}$ (Found: C, 61.66; H, 5.26; N, 8.66, C$_{24}$H$_{25}$N$_3$O$_7$ requires, C, 61.66; H, 5.39; N, 8.99%).

6-[3-(4-Acetyl-3-hydroxy-2-n-propylphenoxy)-2-hydroxypropan-1-yloxy]5-methyl-9-oxo-1H,9H-benzopyrano-[2,3-d]-v-triazole, mono sodium salt To a warm solution of the above compound (0.5 g) in ethanol (50 ml) was added dropwise a standard 1.0 M sodium hydroxide solution (0.90 ml) to a final pH of 8. The solvent was evaporated in vacuo and the residual foam recrystallised from isopropanol to yield 0.387 g (74%) of crystalline product.

$\nu_{max}$ (mull): 1608, 1630, 3250 (very broad) cm$^{-1}$.

$\delta$DMSO-d$_6$: 0.79 (3H, t, J 7 Hz); 1.41 (2H, m); 2.31 (3H, s); 2.52 (2H, obscured by DMSO); 2.60 (3H, s); 4.24 (5H, bs); 5.47 (1H, bs, exchanged D$_2$O); 6.70 (1H, d, J 9 Hz); 7.07 (1H, d, J 9 Hz); 7.81 (1H, d, J 9 Hz); 8.01 (1H, d, J 9 Hz); 12.80 (1H, s, exchanged D$_2$O).

Found: C, 58.58; H, 5.12; N, 8.07; (C$_{24}$H$_{24}$NaN$_3$O$_7$ requires: C, 58.89; H, 4.94; N, 8.59%)

DESCRIPTION 3

(a) Ethyl 1-benzyl-5-(3-methoxyphenoxy)-v-triazole-4-carboxylate

A 50% dispersion of sodium hydride in mineral oil, (6.40 g, 0.13 mole), was added to a stirred solution of 3-methoxyphenol,(16.40 g, 0.13 mole) in dry DMF, (500 ml), and to the resulting sodium salt was added ethyl 1-benzyl-5-chloro-v-triazole-4-carboxylate, (35.0 g, 0.13 mole). The reaction mixture was heated with stirring at 70° C. for 21 hours and cooled.

Removal of the DMF in vacuo gave a brown oil which was taken up in ether, washed with 1 M sodium hydroxide solution, water, and brine and dried (MgSO$_4$). Evaporation gave a red oil, which crystallized on trituration with ether/petrol ether [bp 40°-60° C.] (1:1).

Recrystallization from ether/petrol ether [bp 60°-80° C.] gave 33.75 g (53%) of product of mp 52°-53° C.

Found; C, 64.51; H, 5.27; N, 12.05; C$_{19}$H$_{19}$N$_3$O$_4$ requires C, 64.58; H, 5.42; N, 11.89%

(b) Ethyl 5-(3-methoxyphenoxy)-1H-v-triazole-4-carboxylate

Hydrogenolysis of a solution of ethyl 1-benzyl-5-(3-methoxyphenoxy)-v-triazole-4-carboxylate, (17.27 g) in ethanol, (300 ml), over 10% palladium on charcoal at 100° C. and 1000 psi resulted in clean removal of the N-benzyl group in 2.5 hours. On cooling and removal of the catalyst by filtration, evaporation of the solvent gave an orange oil which crystalized on trituration.

Recrystallization from ethanol/water gave 9.16 g, (71%), of product of mp 104°-5° C.

Found C, 54.92, H 4.88; N, 15.71, $C_{12}H_{13}N_3O_4$; requires C, 54.75; H, 4.98; N, 15.96%.

(c) 5-(3-Methoxyphenoxy)-1H-v-triazole-4-carboxylic acid

Hydrolysis of ethyl 5-(3-methoxyphenoxy)-1H-v-triazole-4-carboxylate, (9.10 g), with 5% aqueous sodium hydroxide (110 ml), at 80° C. for 1 hour afforded the acid which was isolated after acidification of the cooled, (0° C.), solution. Recrystallization from ethylacetate/petrol ether[bp 40°-60° C.]gave 6.20 g (76%) of material of mp 133°-4° C. (dec).

Found; C, 51.31; H. 3.60; H, 17.88, $C_{10}H_9N_3O_4$ requires C, 51.07, H, 3.86, H, 17.86%

(d)
6-Methoxy-9-oxo-1H,9H-benzopyrano[2,3-d]-v-triazole
and
8-methoxy-9-oxo-1H,9H-benzopyrano[2,3-d]-v-triazole

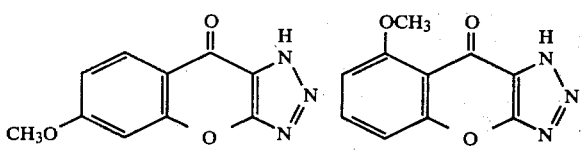

To a solution of phosphorus pentoxide (40 g) in 98% methanesulphonic acid (100 g), at 80° C. was added 5-(3-methoxyphenoxy)-1H-v-triazole-4-carboxylic acid (5.50 g) with vigorous stirring and the brown solution maintained at 80° C. After 4 hours hplc monitoring showed the absence of starting material. The solution was cooled, diluted with ice water and left to stand overnight. The pink precipitate was collected by filtration to yield 4.1 g, (75%), of the 6-methoxy and 8-methoxy mixed isomers in the ratio 2:1 respectively. The pure isomers could be separated by fractional crystallization from ethanol.

Data of pure 6-methoxy isomer mp 270°-1° C. (dec)
vmax (mull) 1585, 1615, 1640, 1655 cm$^{-1}$
$\delta$DMSOd$_6$, 3.94 (3H, s), 7.09 (1H, dd, J 2 & 7 Hz) 7.27 (1H, d, J 2 Hz), 8.12 (1H, d, J 7 Hz), Found; C, 54.97; H, 3.54; N, 19.51; $C_{10}H_7N_3O_3$ requires C, 55.30; H, 3.25; N, 19.35%
M+ =217.0494 ($C_{10}H_7N_3O_3$)

Data of pure 8-methoxy isomer mp 258°-60° C.
vmax (mull) 1550, 1610, 1658, 1670, 3130 cm$^{-1}$
$\delta$ DMSOd$_6$; 3.92 (3H, s), 7.06 (1H, dd J 8 Hz), 7.24 (1H, dd J 8 Hz), 7.77 (1H, t, J 8 Hz)

Found C, 55.31, H, 3.29, N, 19.64; $C_{10}H_7N_3O_3$ requires C, 55.30, H, 3.25, N,19.35%
M+217.0487 ($C_{10}H_7N_3O_3$)

(e)
6-Hydroxy-9-oxo-1H,9H-benzopyrano[2,3-d]-v-triazole

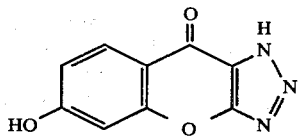

A 50% dispersion of sodium hydride in mineral oil (4.30 g, 0.09 M), was added to a stirred solution of ethanethiol (5.46 g, 0.09 M), in dry DMF, (90 ml), and to the resulting sodium salt was added 6-methoxy-9-oxo-1H,9H-benzopyrano[2,3-d]-v-triazole (2.25 g, 0.01 M). The mixture was heated, with stirring to 120° C. for 1.5 hours when TLC showed no starting material. The reaction was cooled and poured into ice water. The product was isolated by acidification of the solution. Recrystallization from aqueous DMF gave 1.80 g, (85%), of material
mp 300° C. (dec)
vmax (mull) 1550, 1580, 1650, 3215 cm$^{-1}$
$\delta$ DMSOd$_6$; 6.94 (2H, m), 8.08 (1H, d, J 9 Hz), 11.01 (1H, s, exchanges with D$_2$O),
M+ =203.0337 ($C_9H_5N_3O_3$)

(f)
6-Hydroxy-N-(4-methoxybenzyl)-9-oxo-9H-benzopyrano[2,3-d]-v-triazole

6-Hydroxy-9-oxo-1H,9H-benzopyrano[2,3-d]-v-triazole, (2.37 g, 0.012 M) was dissolved in dry DMF, (50 ml) was treated with anhydrous potassium carbonate, (3.23 g, 0.023 M) and 4-methoxybenzyl chloride (1.80 g, 0.012 M). The mixture was stirred at room temperature for 24 hours after which time the solvent was removed in vacuo. The residue was dissolved in water, acidified with 5 M HCl and extracted with ethyl acetate. After evaporation of the dried, organic phase, the resulting yellow oil was chromatographed to give 2.20 g (58%) of a 1:1 ratio of mixed isomers believed to be N-1 and N-2 derivatives. The methylene signals in the NMR spectrum occurred at $\delta$ (DMSOd$_6$) 5.78 and 5.90 ppm. The pure N-1 isomer could be separated by careful chromatography.
N-1 isomer mp 230°-1° C.
vmax (mull) 1605, 1640, 1660 cm$^{-1}$
$\delta$ (DMSOd$_6$) 3.74 (3H, s), 5.90 (2H, s), 6.93 (2H, m), 7.13 (4H, ABq $\Delta$u33 Hz J 9 Hz), 8.05 (1H, d, J 9 Hz), 11.14 (1H, s, exchanges D$_2$O)
Found; C, 63.63, H, 4.40, N, 13.39; $C_{17}H_3N_3O_4$ requires C, 63.15, H, 4.05, N 13.00%)

(g)
6-[3-(4-Acetyl-3-hydroxy-2-n-propylphenoxy)-2-hydroxypropan-1-yloxy]-N-(4-methoxybenzyl)-9-oxo-9H-benzopyrano[2,3-d]-v-triazoles A solution of the above isomeric mixture (500 mg 1.55 mmole), and 4-(2,3-epoxypropoxy)-2-hydroxy-3-n-propyl acetophenone, (464 mg, 1.90 mmole) in dry dimethylformamide, (25 ml) was treated with Triton B, (10 drops), and the orange solution stirred at 140° C. for 5.5 hours, after which time TLC showed the reaction was complete. On cooling, the solvent was evaporated in vacuo and the red residue partitioned between ethyl acetate and water. The organic phase was separated, washed with brine, dried, (MgSO$_4$), and evaporated to dryness in vacuo. The red residue was chromatographed on silica eluting with CHCl₃ to give 612 mg (69%) of the mixed isomers as a colourless oil. The methylene signals in the NMR occurred at δ (CDCl₃) 5.62 (N-2 isomer) and 5.91 (N-1 isomer).

Pure N-1 isomer was obtained in a separate experiment using pure triazole from 3f.

Data of pure N-1 isomer mp 172°-3° C. (EtOH)

$\nu$max (mull) 1610, 1658, 3500 cm$^{-1}$

δ (CDCl₃) 0.92 (3H, t, J 7.5 Hz), 1.53 (2H, m), 2.57 (3H, s), 2.62 (2H, m), 3.77 (3H, s), 4.31 (5H, m), 5.91 (2H, s), 6.47 (1H, d, J 9 Hz), 6.96 (2H, m), 7.18 (4H, ABq Δ$\nu$=52 Hz, J 9 Hz), 7.56 (1H, d, obscured) 8.25 (1H, d, J 9 Hz), 12.73 (1H, s)

Found C, 64.71; H, 5.87; N, 7.38; $C_{31}H_{31}N_3O_8$ requires C, 64.91; H, 5.45; N, 7.33%)

EXAMPLE 3

6-[3-(4-Acetyl-3-hydroxy-2-n-propylphenoxy)-2-hydroxypropan-1-yloxy]-9-oxo-1H,9H-benzopyrano[2,3-d]-v-triazole

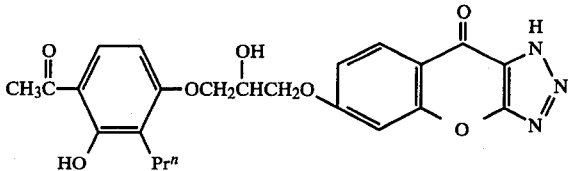

A solution of the mixed isomers of 6-[3-(4-acetyl-3-hydroxy-2-n-propylphenoxy)-2-hydroxypropan-1-yloxy]N-(4-methoxybenzyl)9-oxo-9H-benzopyrano[2,3-d]-v-triazole (590 mg, 1.03 mmole), in trifluoroacetic acid (10 ml) was stirred at 65° C. (oil bath temperature). After 5 hours HPLC showed no starting material left. The reaction was cooled and evaporated in vacuo to dryness. The residue was chromatographed on silica gel, eluting with CHCl₃ to CHCl₃/2% methanol to give 70 mg (17%) of product, mp (EtOH/H₂O) 228°-9° C. (dec)

$\nu$max (mull) 1610, 1650, 3400 cm$^{-1}$

δ (CD₃)₂SO, 0.82 (3H, t, J 7 Hz), 1.43 (2H, m), 3.31 (3H, s), 3.31 (1H, m), 4.25 (4H, m), 5.54 (1H, broad s, exchanged D₂O), 6.69 (1H, d, J 9 Hz), 7.13 (1H, dd J 9 and 2 Hz), 7.32 (1H, d, J 2 Hz), 7.81 (1H, d, J 9 Hz), 8.14 (1H, d, J 9 Hz), 12.80 (1H, s, exchanged D₂O)

Found, C; 59.47; H. 5.74; N, 8.68, $C_{23}H_{23}N_3O_7 0.5$-H₂O requires C, 59.73; H, 5.34; N, 9.09%

Other material was collected with a peak of 1795 cm$^{-1}$ in the infrared spectrum, which suggests a trifluoracetate of the glyceryl side chain.

Alkaline hydrolysis of this yielded a further 85 mg (20%) of product, mp 228°-9° C. (dec).

6-[3-(4-Acetyl-3-hydroxy-2-n-propylphenoxy)-2-hydroxypropan-1-yloxy]-9-oxo-1H,9H-benzopyrano-[2,3-d]-v-triazole sodium salt A warm solution of the above compound (0.158 g) in aqueous ethanol was treated dropwise with standard 1.0 M sodium hydroxide solution (0.34 ml) to a final pH of 8.0. The solvents were evaporated in vacuo and the residue recrystallised from isopropanol to yield 0.121 g (73%) of sodium salt.

$\nu$max (mull): 1575 (weak), 1623, 1663 cm$^{-1}$.

δ DMSO-d₆: 0.85 (3H, t, J 7 Hz); 1.45 (2H, m); 2.52 (2H, obscured by DMSO); 2.59 (3H, s); 4.24 (5H, bs); 5.50 (1H, bs exchange D₂O); 6.71 (1H, d, J 9 Hz); 6.98 (1H, dd, J 9 and 2.5 Hz); 7.12 (1H, d, J 2.5 Hz); 7.83 (1H, d, J 9 Hz); 8.09 (1H, d, J 9 Hz); 12.82 (1H, s, exchanged D₂O).

Found: C, 57.42; H, 4.69; N, 8.50 ($C_{23}H_{22}NaN_3O_7,0.5H_2O$ requires: C, 57.02; H, 4.79; N, 8.67%).

It will be appreciated that of the compounds named on page 8 hereinbefore, compounds (a), (b) and (d) are Examples 1, 2 and 3 hereinbefore.

Compounds (c), (e) and (g) named on page 8 may be prepared in similar manner to that described for Compounds (a), (b) and (d) in the Descriptions and Examples hereinbefore.

DESCRIPTION 4

(a)

8-Hydroxy-9-oxo-1H,9H-benzopyrano-[2,3-d]-v-triazole

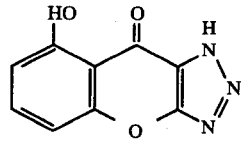

A 50% dispersion of sodium hydride in mineral oil, (3.84 g, 0.08 M) was added to a stirred solution of ethanethiol (5.10 g, 0.08 M), in dry DMF, (100 ml), and to the resulting sodium salt was added 8-methoxy-9-oxo-1H,9H-benzopyrano-[2,3-d]-v-triazole, (2.36 g, 0.011 M) (prepared as in Description 3(d)). The mixture was heated, with stirring to 115° C. for 1.5 hours, when HPLC and TLC showed no starting material. The reaction was cooled, poured into ice water, and the product was isolated by acidification of the solution. Recrystallization from methanol gave 1.18 g, (53%), of pale orange crystals, mp 256°-8° C. (dec), $\nu_{max}$ (mull) 1618, 1638, 3160 cm$^{-1}$.

δ DMSOd₆-6.86 (1H, d, J 8 Hz) 7.14 (1H, d, J 8 Hz), 7.73 (1H, t, J 8 Hz), 12.30 (1H, s, exchanged with D₂O).

Found: C, 53.12; H, 2.60; N, 20.90; $C_9H_5N_3O_3$ requires C, 53.21; H, 2.48; N, 20.69%. M+=203.0319, ($C_9H_5N_3O_3$).

(b)

8-Hydroxy-9-oxo-2-(triphenylmethyl)-9H-benzopyrano[2,3-d]-v-triazole

8-Hydroxy-9-oxo-1H,9H-benzopyrano,[2,3-d]-v-triazole, (0.96 g, 0.0044 M) was dissolved in dry DMF, (40 ml) and treated with anhydrous potassium carbonate, (1.21 g, 0.0088 M), and triphenylmethyl chloride, (1.41 g, 0.0049 M). The mixture was stirred at room temperature overnight after which time the solvent was removed in vacuo. The residue was dissolved in water, acidified with 5 M HCl and the yellow precipitate collected by filtration, washed with water and dried in vacuo. Purification using column chromatography gave 1.51 g (77%) of product, mp 166°-7° C.

$\nu_{max}$ (mull)—1543, 1625, 1650 cm$^{-1}$.

δ CDCl₃-6.80 (1H, d, J 8 Hz), 7.00 (1H, d, J 8 Hz), 7.23 15H, m), 7.55 (1H, t, J 8 Hz) 12.36 (1H, s, exchanged D₂O).

Found: C, 75.26; H, 4.51, N, 9.24, $C_{28}H_{19}N_3O_3$ requires C, 75.49; H, 4.30; N, 9.43%. M+=445 1422 ($C_{28}H_{19}N_3O_8$).

(c)
8-[3-(4-Acetyl-3-hydroxy-2-n-propylphenoxy)-propan-1-yloxy]-9-oxo-2-(triphenylmethyl)-9H-benzopyrano[2,3-d]-v-triazole A solution of the above compound, (1.32 g, 3.0 mmole), 3-(4-acetyl-3-hydroxy-2-n-propylphenoxy)propan-1-ol (0.75 g, 3.0 mmole) and triphenylphosphine, (1.42 g, 5.4 mmoles), in dry THF, (100 ml), was stirred at 20° C. and diethyl azodicarboxylate, (0.94 g, 5.4 mmole), added. After stirring at 20° C. for 1 hour, the reaction was complete by tlc. The solvent was evaporated in vacuo and the orange residue was chromatographed to give a yellow oil which crystallized on boiling with ethanol. Dried in vacuo to yield 1.38 g (68%), of product, mp 161°–2° C.

$\nu_{max}$ (mull) – 1545, 1603, 1623, 1683 cm$^{-1}$.

δ CDCl$_3$-0.82 (3H, t, J 7 Hz), 1.39 (2H, m) 2.33 (2H, t, J 7 Hz), 2.50 (3H, s), 2.56 (2H, t, J 7 Hz), 4.25 (2H, t, J 7 Hz), 4.42 (2H, t, J 7 Hz), 6.55 (1H, d, J 9 Hz) 6.83 (1H, d, J 9 Hz), 7.32 (18H, m).

Found: C, 73.45; H, 5.54; N, 6.04; C$_{42}$H$_{37}$N$_3$O$_6$. 0.5 CH$_3$CH$_2$OH requires C, 73.49; H, 5.93; N, 5.98%.

EXAMPLE 4

8-[3-(4-Acetyl-3-hydroxy-2-n-propylphenoxy)-propan-1-yloxy]-9-oxo-1H,9H-benzopyrano-[2,3-d]-v-triazole

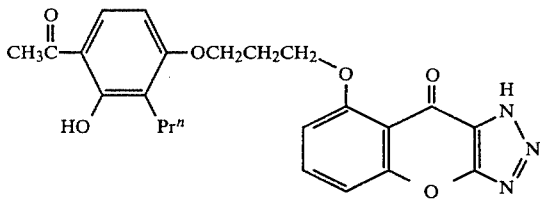

A solution of the above compound, (100 mg, 0.15 mmole), in glacial acetic acid, (2 ml) and concentrated hydrochloric acid, (2 drops), was heated with magnetic stirring at 55° C. After 4 hours, TLC showed the reaction to be complete. The reaction was cooled, poured into water, and the product extracted into ethylacetate. Evaporation of the dried extracts gave an oil which was purified by column chromatography to yield 42 mg (67%) of white solid mp 139°–40° C.

$\nu_{max}$ (mull) 1608, 1630, 1655, 3100 (weak), cm$^{-1}$.

δ DMSO$_{d6}$, 0.82 (3H, t, J 7 Hz), 1.32 (2H, m), 2.28 (2H, m) 2.59 (3H, s), 2.59 (2H, m), 4.29 (2H, t, J 6 Hz), 4.46 (2H, t, J 6 Hz), 6.72 (1H, d, J 9 Hz), 7.06 (1H, d, J 9 Hz), 7.22 (1H, d, J 9 Hz), 7.75 (1H, t, J 9 Hz), 7.80 (1H, d, J 9 Hz), 12.84 (1H, s, exchanged D$_2$O).

Found: C, 63.06; H, 5.01; N, 9.31; C$_{23}$H$_{23}$N$_3$O$_6$ requires C, 63.15; H, 5.30; N, 9.61%.

DESCRIPTION 5

(a)
7-Hydroxy-9-oxo-1H,9H-benzopyrano-[2,3-d]-v-triazole

A 50% dispersion of sodium hydride in mineral oil (0.53 g, 11 mmole) was added to a stirred solution of ethanethiol (0.68 g, 11 mole) in dry DMF (25 ml) and to the resulting sodium salt was added 7-methoxy-9-oxo-1H, 9H-benzopyrano-[2,3-d]-v-triazole (0.32 g, 1.47 mmole). The mixture was heated, with stirring to 120° C. for 7 hours when TLC showed starting material still remaining. A further 5 mmole of sodiumthioethoxide in dry DMF (1 ml) was added and after a further 4 hours the reaction was complete. The reaction was cooled, and poured into ice water. The product was isolated by acidification of the solution and extraction with ethyl acetate. Evaporation of the dried extracts yielded a red oil. Purification using column chromatography and recrystallisation from aqueous DMF gave 0.15 g (51%) of product mp >300° C.

$\nu_{max}$ (mull): 1555, 1590, 1638, 1663, 2740 (weak), 3100 (broad) cm$^{-1}$.

δ, DMSO-d$_6$: 7.25 (1H, dd, J 9 and 2.5 Hz); 7.50 (1H, d, J 2.5 Hz); 7.60 (1H, d, J 9 Hz); 10.00 (1H, broad s, exchanged D$_2$O).

Found: C, 52.94; H, 2.18; N, 20.45; C$_9$H$_5$N$_3$O$_3$ requires C, 53.21; H, 2.48; L N, 20.69%. M$^+$ = 203.0328 (C$_9$H$_5$N$_3$O$_3$).

(b)
7-Hydroxy-9-oxo-2-(triphenylmethyl)-9H-benzopyrano-[2,3-d]-v-triazole

7-Hydroxy-9-oxo-1H,9H-benzopyrano-[2,3-d]-v-triazole (137 mg, 0.67 mmole) was dissolved in dry DMF (10 ml) and treated with anhydrous potassium carbonate (140 mg, 1.0 mmole) and triphenylmethyl chloride (196 mg, 0.67 mmole). The mixture was stirred at room temperature for 24 hours, after which time the solvent was evaporated in vacuo. The residue was suspended in water, acidified with 5 M HCl and the cream precipitate filtered off and dried in vacuo. Purification using column chromatography gave 133 mg (45%) of product mp 266°–7° C. (dec).

$\nu_{max}$ (mull): 1623, 1670, 1683 cm$^{-1}$.

δ, DMSO-d$_6$: 7.25 (17H, m); 7.78 (1H, d, J 2.5 Hz); 9.39 (1H, s).

Found: C, 73.68; H, 4.78; N, 9.69. C$_{28}$H$_{19}$N$_3$O$_3$.0.5 (CH$_3$)$_2$NCHO requires: C, 73.51; H, 4.70; N, 10.16%. M$^+$ = 445.1415 (C$_{28}$H$_{19}$N$_3$O$_3$).

(c)
7-[3-(4-Acetyl-3-hydroxy-2-n-propylphenoxy)-propan-1-yloxy]-9-oxo-2-(triphenylmethyl)-9H-benzopyrano-[2,3-d]-v-triazole A solution of the above compound (91 mg, 0.20 mmole), 3-(4-acetyl-3-hydroxy-2-n-propylphenoxy)-propan-1-ol (52 mg, 0.20 mmole), and triphenylphosphine (79 mg, 0.30 mmole) in dry THF (10 ml) was mechanically stirred at 20° C. and diethyl azodicarboxylate (52 mg, 0.30 mmole) added. After stirring at 20° C. for 1 hour, the reaction was complete by TLC. The solvent was evaporated to dryness in vacuo and the yellow residue boiled in ethanol. On cooling the white solid which crystallised out was collected by filtration and dried in vacuo to yield 74 mg (37%) of product, of indistinct melting point.

$\nu_{max}$ (mull): 1545, 1625, 16683 cm$^{-1}$.

δ CDCl$_3$: 0.96 (3H, t, J 7 Hz); 1.55 (2H, m); 2.33 (4H, m); 2.54 (3H, m); 4.25 (4H, m); 6.47 (1H, d, J 9 Hz); 7.50 (19H, m); 12.70 (1H, s)

M$^+$ = 679.2705 (C$_{42}$H$_{37}$N$_3$O$_6$).

EXAMPLE 5

7-[3-(4-Acetyl-3-hydroxy-2-n-propylphenoxy)-propan-1-yloxy]-9-oxo-1H,9H-benzopyrano-[2,3-d]-v-triazole

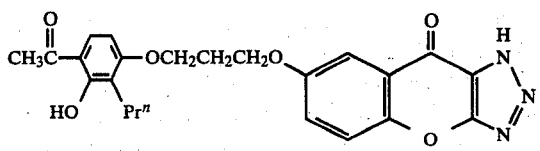

A solution of the above compound (39 mg, 0.057 mmole) in glacial acetic acid (2 ml) containing concentrated hydrochloric acid (1 drop) was heated with magnetic stirring at 65° C. for 3 hours after which time HPLC showed the absence of starting material. The reaction was cooled and evaporated in vacuo. The white residue was washed with water and dried in vacuo. The product was purified by column chromatography to yield 10 mg (40%) of white solid mp 168°–70° C. (dec).

$\nu_{max}$ (mull): 1555, 1590, 1620, 1690, 3080 (weak) 3140 (weak) cm$^{-1}$.

δ DMSO-d$_6$: 0.82 (3H, t, J 7.5 Hz); 1.52 (2H, m); 2.30 (2H, m); 2.55 (2H, m obscured by DMSO); 2.57 (3H, s); 4.30 (4H, t, J 6 Hz); 6.68 (1H, d, J 9 Hz); 7.65 (4H, m); 12.80 (1H, s).

M+ =437.1582 (C$_{23}$H$_{23}$N$_3$O$_6$)

DESCRIPTION 6

(a) 2-Allyl-3-methoxyphenol and 2-allyl-5-methoxyphenol

A solution of allyl 3-methoxyphenyl ether (230 g, 1.40 mole; W. N. White and C. D. Slater, J Org Chem, 26, 3631-8 (1961)) in N,N-dimethylaniline (150 ml) was refluxed in an atmosphere of nitrogen for 4 hours. The orange solution was cooled, diluted with petroleum ether [bp 60°–80° C.] and washed with 5 M sulphuric acid. The organic phase was extracted with 2.5 M sodium hydroxide, and the aqueous extracts re-acidified with 5 M hydrochloric acid. The isomeric mixture of phenols was extracted with ethyl acetate, dried (MgSO$_4$) and evaporated in vacuo to yield 144 g (63%) of brown oil the NMR of which showed 60% of 2-allyl-5-methoxy phenol, 40% of the other isomer. The two products could be separated by careful chromatography using silica gel, eluting with CH$_2$Cl$_2$/petroleum ether (bp 60°–80°) [1:1] to yield the faster running 2-allyl-3-methoxyphenol as a colourless oil, $\nu_{max}$ (film): 1598, 1610, 1637 (shoulder) 3475 cm$^{-1}$.

δ CDCl$_3$: 3.40 (2H, m); 3.80 (3H, s); 5.10 (3H, m); 5.95 (1H, m); 6.47 (2H, d, J 9 Hz); 7.30 (1H, t, J 9 Hz), followed by the slower running 2-allyl-5-methoxyphenol as a pale brown oil, $\nu_{max}$ (film): 1598, 1620, 1635 (weak) 3410 cm$^{-1}$.

δ CDCl$_3$: 3.31 (2H, m); 3.78 (3H, s); 5.23 (3H, m); 6.03 (1H, m); 6.40 (1H, bs); 6.47 (1H, dd, J 2 Hz and 9 Hz); 6.98 (1H, d, J 9 Hz).

(b) Ethyl 5-(2-allyl-3-methoxyphenoxy)-1-(4-methoxybenzyl)-v-triazole-4-carboxylate A 50% dispersion of sodium hydride in mineral oil (3.90 g, 0.08 M) was added to a stirred solution of 2-allyl-3-methoxyphenol (13.32 g, 0.08 M) in dry DMF (300 ml) and to the resulting sodium salt was added ethyl-5-chloro-1-(4-methoxybenzyl)-v-triazole-4-carboxylate (24.0 g, 0.08 M). The reaction mixture was heated with stirring at 80° C. for 18 hours and then cooled. Removal of the DMF in vacuo gave a red oil which was taken up in ethyl acetate, washed with water, and dried (MgSO$_4$). Evaporation gave an oil which crystallised on trituration. Recrystallisation from ethanol/petroleum ether [bp 60°–80° C.] gave 21.58 g (64%) of product, mp 109°–10° C.

$\nu_{max}$ (mull): 1570, 1595, 1605, 1715 cm$^{-1}$.

δ CDCl$_3$: 1.02 (3H, t, J 6 Hz); 3.48 (2H, m); 3.73 (3H, s); 3.83 (3H, s); 4.09 (2H, q, J 6 Hz); 4.97 (2H, m); 5.28 (2H, s); 5.87 (1H, d, J 9 Hz); 5.90 (1H, m); 6.61 (1H, d, J 9 Hz); 6.92 (1H, t, J 9 Hz); 6.93 (4H, AB quartet Δν=39 Hz, J 9 Hz).

Found: C, 64.87; H, 5.57; N, 9.86. C$_{23}$H$_{25}$N$_3$O$_5$ requires: C, 65.25; H, 5.95; N, 9.92%. M+ =423.1822 (C$_{23}$H$_{25}$N$_3$O$_5$).

(c) Ethyl 5-(3-methoxy-2-n-propylphenoxy)-1H-v-triazole-4-carboxylate

Hydrogenolysis of a solution of the above compound (1.0 g) in ethanol (300 ml) over 10% palladium on charcoal at 100° C. and 1 000 psi resulted in reduction of the allyl double bond and clean removal of the N-(4-methoxybenzyl) group within 10 hours. On cooling and removal of the catalyst by filtration, evaporation in vacuo, gave an oil which was purified by column chromatography to yield 0.53 g (63%) of product, a white solid, mp 97°–9° C.

$\nu_{max}$ (mull): 1585, 1603, 1690, 3180 cm$^{-1}$.

δ (CDCl$_3$): 0.87 (3H, t, J 7 Hz); 1.26 (3H, t, J 7 Hz); 1.50 (2H, m); 2.63 (2H, t, J 7 Hz); 3.82 (3H, s); 4.33 (2H, q, J 7 Hz); 6.63 (2H, m); 7.06 (1H, t, J 8 Hz).

Found: C, 58.62; H, 6.42; N, 13.54; C$_{15}$H$_{19}$N$_3$O$_4$ requires C, 59.00; H, 6.27; N, 13.76%.

M+ =305.1388 (C$_{15}$H$_{19}$N$_3$O$_4$).

(d) 5-(3-Methoxy-2-n-propylphenoxy)-1H-v-triazole-4-carboxylic acid

Hydrolysis of ethyl 5-(3-methoxy-2-n-propylphenoxy)-1H-v-triazole-4-carboxylate (1.06 g) with 1.0 M sodium hydroxide solution (15 ml) at 70° C. over 2 hours, afforded the acid which was isolated by acidification of the cooled solution. Recrystallisation from aqueous ethanol gave 0.84 g (88%) of product, mp 146°–7° C. (dec).

$\nu_{max}$ (mull): 1595, 1608, 1695, 3200 cm$^{-1}$.

δ DMSO-d$_6$: 0.80 (3H, t, J 6 Hz); 1.43 (2H, m); 2.52 (2H, m); 3.79 (1H, s); 6.48 (1H, d, J 8 Hz); 6.73 (1H, d, J 8 Hz); 7.08 (1H, t, J 8 Hz).

Found: C, 56.63; H, 5.47; N, 14.81. C$_{13}$H$_{15}$N$_3$O$_4$ requires: C, 56.31; H, 5.45; N, 15.16%.

M+ =277.1052 (C$_{13}$H$_{15}$N$_3$O$_4$).

(e) 6-Methoxy-9-oxo-5-n-propyl-1H,9H-benzopyrano[2,3-d]-v-triazole

To a solution of phosphoric oxide (8.0 g) in 98% methanesulphonic acid (20 ml), at 80° C. was added 5-(3-methoxy-2-n-propylphenoxy)-1H-v-triazole-4-carboxylic acid (0.94 g, 3.4 mmole) with stirring and the pale red solution maintained at 80° C. for 3 hours, after which time HPLC showed a trace of starting material remaining. The reaction was cooled, diluted with water (100 ml), and the resultant brick red precipitate filtered off, washed with water and dried in vacuo. Recrystallisation from aqueous ethanol afforded 0.40 g (46%) of product as a cream solid, mp 220°-2° C. (dec).

$\nu_{max}$ (mull): 1610, 1660 cm$^{-1}$.

δ DMSO-d$_6$: 0.94 (3H, t, J 7 Hz); 1.60 (2H, m); 2.81 (2H, t, J 7 Hz); 3.98 (3H, s); 7.21 (1H, d, J 9 Hz); 8.08 (1H, d, J 9 Hz).

Found: C, 60.10; H, 5.03; N, 16.10. C$_{13}$H$_{13}$N$_3$O$_3$ requires: C, 60.22; H, 5.05; N, 16.21%. M$^+$=259.0956 (C$_{13}$H$_{13}$N$_3$O$_3$).

(f)
6-Hydroxy-9-oxo-5-n-propyl-1H,9H-benzopyrano[2,3-d]-v-triazole

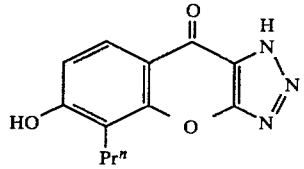

A 50% dispersion of sodium hydride in mineral oil (12.20 g, 0.25 M) was added to a stirred solution of ethanethiol (15.76 g, 0.25 M) in dry DMF (250 ml) and to the resulting sodium salt was added 6-methoxy-9-oxo-5-n-propyl-1H,9H-benzopyrano-[2,3-d]-v-triazole (9.40 g, 0.036 M). The mixture was heated with stirring to 120° C. for 0.75 hours when HPLC showed no starting material. The reaction was cooled, evaporated in vacuo to dryness and the residue poured into water. The product was isolated by acidification of the solution. Recrystallisation from ethanol gave 5.84 g (66%) of pale yellow crystals, mp 283°-4° C. (dec).

$\nu_{max}$ (mull): 1550, 1560, 1605, 1640, 3130 cm$^{-1}$.

δ DMSO-d$_6$: 1.00 (3H, t, J 7 Hz); 1.64 (2H, m); 2.84 (2H, t, J 7 Hz); 7.05 (1H, d, J 9 Hz); 7.98 (1H, d, J 9 Hz); 11.00 (1H, bs, exchanged D$_2$O); 16.45 (1H, bs, exchanged D$_2$O).

Found: C, 58.55; H, 4.74; N, 17.03. (C$_{12}$H$_{11}$N$_3$O$_3$ requires: C, 58.77; H, 4.52; N, 17.14%) M$^+$=245.0799 (C$_{12}$H$_{11}$N$_3$O$_3$).

(g)
6-Hydroxy-9-oxo-5-n-propyl-2-(triphenylmethyl)-9H-benzopyrano[2,3-d]-v-triazole 6-Hyroxy-9-oxo-5-n-propyl-1H,9H-benzopyrano[2,3-d]-v-triazole (2.0 g, 8.2 mmole) was dissolved in dry DMF (50 ml) and treated with anhydrous potassium carbonate (1.67 g, 12 mmole) and triphenylmethylchloride (2.35 g, 8.2 mmole). The mixture was stirred at room temperature overnight after which time the solvent was removed in vacuo. The residue was dissolved in water, acidified with 5 M HCl and the pale yellow precipitate extracted several times with chloroform. The dried (MgSO$_4$) extracts were evaporated in vacuo and the yellow residue subjected to column chromatography to yield 1.73 g (44%) of product mp 221°-2° C. (dec).

$\nu_{max}$(mull): 1555, 1600, 1605, 1660, 3330 cm$^{-1}$.

δ DMSO-d$_6$: 0.93 (3H, t, J 7 Hz); 1.56 (2H, m); 2.78 (2H, t, J 7 Hz); 7.01 (1H, d, J 9 Hz, partially obscured); 7.28 (15H, m); 7.94 (1H, d, J 9 Hz); 10.93 (1H, bs, exchanged D$_2$O).

M$^+$=489.1889 (C$_{31}$H$_{25}$N$_3$O$_3$).

(h)
6-[3-(4-Acetyl-3-hydroxy-2-n-propylphenoxy)-propan-1-yloxy]-9-oxo-5-n-propyl-2-(triphenylmethyl)-9H-benzopyrano-[2,3-d]-v-triazole A solution of the above compound (1.0 g, 2.1 mmole), 3-(4-acetyl-3-hydroxy-2-n-propylphenoxy)propan-1-ol (0.52 g, 2.1 mmole) and triphenylphosphine (0.97 g, 3.7 mmole) in dry THF (50 ml) was stirred at 20° C. and diethyl azodicarboxylate (0.64 g, 3.7 mmole) added. After stirring at 20° C. for 1 hour, the reaction was completed by TLC. The solvent was evaporated in vacuo and the pale yellow residue chromatographed on silica gel, eluting with CHCl$_3$/petroleum ether [bp 60°-80° C.] to yield 1.07 g (71%) of product as a white foam. Crystallisation from hot ethanol gave a white solid mp 181°-3° C.

$\nu_{max}$ (mull): 1540, 1605, 1625, 1670 cm$^{-1}$.

δ DMSO-d$_6$: 0.91 (6H, m); 1.46 (4H, m); 2.33 (2H, t, J 6 Hz); 2.54 (3H, s); 2.62 (2H, t, J 6 Hz); 2.85 (2H, t, J 6 Hz); 4.24 (2H, t, J 6 Hz); 4.32 (2H, t, J 6 Hz); 6.42 (1H, d, J 9 Hz); 6.98 (1H, d, J 9 Hz); 7.27 (15H, m); 7.58 (1H, d, J 9 Hz); 8.25 (1H, d, J 9 Hz); 12.72 (1H, s).

Found: C, 74.53; H, 6.00; N, 6.00. (C$_{45}$H$_{43}$N$_3$O$_6$ requires: C, 74.90; H, 6.01; N, 5.82%).

M$^+$=721.3150 (C$_{45}$H$_{43}$N$_3$O$_6$).

EXAMPLE 6

6-[3-(4-Acetyl-3-hydroxy-2-n-propylphenoxy)-propan-1-yloxy]-9-oxo-5-n-propyl-1H,9H-benzopyrano-[2,3-d]-v-triazole

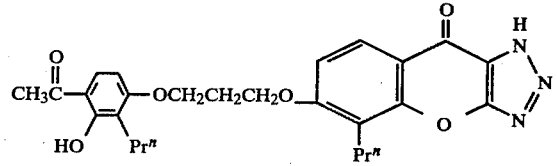

A solution of the above compound (300 mg, 0.42 mmole) in glacial acetic acid (20 ml) and concentrated hydrochloric acid (0.5 ml) was heated with magnetic stirring at 70° C. After 6 hours TLC showed the reaction to be complete. The reaction was cooled, the solvent evaporated in vacuo and water (20 ml), added. The product was extracted into ethyl acetate. Evaporation of the dried extracts gave a cream solid which was triturated with dichloromethane and filtered to yield 75 mg (38%) of the product, mp 216°-17° C. dec. A second crop was obtained by column chromatography of the filtrate using SiO$_2$ eluting with CHCl$_3$ to yield 70 mg (35%) of product. Recrystallisation from ethanol did not alter the melting point.

$\nu_{max}$ (mull): 1560, 1610, 1680 cm$^{-1}$.

δ DMSO-d$_6$: 0.78 (3H, t, J 7 Hz); 0.88 (3H, t, J 7 Hz); 1.45 (4H, m); 2.27 (2H, t, J 7 Hz); 2.49 (2H, m, obscured); 2.58 (3H, s); 2.81 (2H, t, J 7 Hz); 4.30 (4H, m); 6.67 (1H, d, J 9 Hz); 7.23 (1H, d, J 9 Hz); 7.80 (1H, d, J 9 Hz); 8.10 (1H, d, J 9 Hz); 12.82 (1H, s).

Found: C, 64.60; H, 6.04; N, 8.41. (C$_{26}$H$_{29}$N$_3$O$_6$, 0.25H$_2$O requires: C, 64.53; H, 6.16; N, 8.60%).

M$^+$=479.2042 (C$_{26}$H$_{29}$N$_3$O$_6$).

6-[3-(4-Acetyl-3-hydroxy-2-n-propylphenoxy)-propan-1-yloxy]-9-oxo-5-n-propyl-1H,9H-benzopyrano-[2,3-d]-v-triazole mono-sodium salt A warm solution of the above compound (100 mg) in aqueous DMF was treated with standard 0.1 M sodium hydroxide solution (2.1 ml) dropwise after which the pH of the solution was 7.5. The solvent was removed in vacuo and the colourless oil recrystallised from isopropanol to yield 72 mg (70%) of product.

$\nu_{max}$ (mull): 1550, 1605, 1625 cm$^{-1}$.

$\delta$ DMSO-d$_6$: 0.80 (3H, t, J 7 Hz); 0.89 (3H, t, J 7 Hz); 1.49 (4H, m); 2.30 (2H, m); 2.50 (2H, m); 2.57 (3H, s); 2.85 (2H, t, J 7 Hz); 4.31 (4H, t, J 6 Hz); 6.69 (1H, d, J 9 Hz); 7.09 (1H, d, J 9 Hz); 7.82 (1H, d, J 9 Hz); 8.02 (1H, d, J 9 Hz); 12.81 (1H, s, exchanged D$_2$O).

DESCRIPTION 7

(a) Ethyl 5-(2-allyl-5-methoxyphenoxy)-1-benzyl-v-triazole-4-carboxylate

To a solution of 2-allyl-5-methoxyphenol (15.41 g, 0.094 mmole) in dry DMF (150 ml) was added a 50% dispersion of sodium hydride in mineral oil (4.51 g, 0.094 mole) and the mixture stirred at ambient temperature for 15 minutes to complete formation of the sodium salt. Ethyl 1-benzyl-5-chloro-v-triazole-4-carboxylate (27.8 g, 0.094 mole) was added and the reaction mixture stirred at 70°-80° C. for 16 hours. After cooling, the solvent was removed in vacuo and the product was partitioned between water and ethyl acetate. The organic phase was washed with dilute sodium hydroxide, water and brine and dried (MgSO$_4$). Evaporation and chromatography of the residual oil on silica with chloroform elution gave 32.54 g (88%) of the pure product. Recrystallisation from toluene-petroleum ether [bp 40°-60°] gave a white solid of mp 55°-56° C.

$\nu_{max}$ (mull) 1738, 1620, 1555, 1505 cm$^{-1}$.

$\delta$ (CDCl$_3$): 1.08 (3H, t, J 7.3 Hz); 3.41 (2H, d, J 5.4 Hz); 3.52 (3H, s); 4.18 (2H, q, J 7.3 Hz); 4.98 (1H, d); 5.15 (1H, d); 5.40 (1H, s); 5.78 (1H, d, J 2.7 Hz); 6.00 (1H, complex m); 6.60 (1H, d.d, J 8.4 Hz, 2.7 Hz); 7.14 (1H, d, J 8.4 Hz); 7.25 (5H, s).

Found: C, 67.12; H, 6.00; N, 10.73. C$_{22}$H$_{23}$N$_3$O$_4$ requires: C, 67.16; H, 5.89; N, 10.68%.

(b) Ethyl 5-(5-methoxy-2-n-propylphenoxy)-1H-v-triazole-4-carboxylate

Hydrogenolysis of a solution of ethyl 5-(2-allyl-5-methoxyphenoxy)-1-benzyl-v-triazole-4-carboxylate (30 g) in ethanol (300 ml) over 10% palladinized charcoal (1 g) at 100° C. and 1 000 psi gave the title compound after 5 hours. Filtration and evaporation of the solution gave an oil which was purified on silica chromatography eluting with chloroform to give 22.73 g (98%) of product as a pale yellow oil.

$\nu_{max}$ (film): 3200, 1720, 1620 cm$^{-1}$.

$\delta$ (CDCl$_3$): 0.92 (3H, t, J 7 Hz); 1.32 (3H, t, J 7.3 Hz); 1.60 (2H, sextet, J 8 Hz); 2.60 (2H, t, J 8 Hz); 3.77 (3H, s); 4.41 (2H, q, J 7.3 Hz); 6.65 (1H, d, J 2.7 Hz); 6.70 (1H, d.d, 8.4 Hz, 2.7 Hz); 7.15 (1H, d, J 8.4 Hz); 9.5 (1H, broad exchangeable).

(c) 5-(5-Methoxy-2-n-propylphenoxy)-1H-v-triazole-4-carboxylic acid

A solution of ethyl 5-(5-methoxy-2-n-propylphenoxy)-1H-v-triazole-4-carboxylate (22 g, 0.072 mole) in 1 M aqueous sodium hydroxide (330 ml) was stirred at 70° C. for 2 hours, cooled and washed once with ethyl acetate. The aqueous phase was brought of pH 1 at 0° C. and the precipitated oil extracted into ethyl acetate. The dried extracts were evaporated to give 19.79 g (98%) of crude material. Trituration with toluene-ether followed by petroleum ether [bp 40°-60°] gave 12.56 g of compound of mp 112°-3° C. (dec). Chromatography of the concentrated mother liquors on silica eluting with chloroform then 10% methanol in chloroform gave a further 2.76 g of material. Recrystallisation from ethyl acetate/petroleum ether gave mp 113°-4° C.

$\nu_{max}$ (mull): 3170, 2650 (broad), 1720, 1620, 1530, 1505 cm$^{-1}$.

$\delta$ (DMSO-d$_6$): 0.88 (3H, t, J 6 Hz); 1.55 (2H, sextet, J 6 Hz); 2.56 (2H, t, J 6 Hz); 3.70 (3H, s); 6.57 (1H, d, J 2 Hz); 6.73 (1H, d.d, J 2 Hz, 8 Hz); 7.22 (1H, d, J 8 Hz); 14.3 (2H, broad exchangeable signal).

Found: C, 55.97; H, 5.52; N, 14.92. C$_{13}$H$_{15}$N$_3$O$_4$ requires: C, 56.31; H, 5.45; N, 15.16%.

(d) 8-Methoxy-9-oxo-5-n-propyl-1H,9H-benzopyrano[2,3-d]-v-triazole

To a solution of phosphoric oxide (8.0 g) in 98% methanesulphonic acid (20 ml) was added finely powdered 5-(5-methoxy-2-n-propylphenoxy)-1H-v-triazole-4-carboxylic acid (0.94 g, 3.4 mmole) and the mixture was stirred at 80° C. for 1.5 hours when no acid remained. The red solution was cooled and diluted to 200 ml with water. The bulk of the acidic solution was neutralized and the precipitated solid filtered off and recrystallised from ethanol to give 0.62 g (70%) of title compound of mp 229°-231° C. (dec).

$\nu_{max}$ (mull): 3050 (broad), 1670, 1597, 1530 cm$^{-1}$.

$\delta$ (DMSO-d$_6$): 0.96 (3H, t, J 7 Hz); 1.66 (2H, sextet, J 7 Hz); 2.77 (2H, t, J 7.5 Hz); 3.92 (3H, s); 6.99 (1H, d, J 9 Hz); 7.62 (1H, d, J 9 Hz).

Found: C, 60.18; H, 5.02; N, 16.13. C$_{13}$H$_{13}$N$_3$O$_3$ requires: C, 60.22; H, 5.05; N, 16.21%.

(e) 8-Hydroxy-9-oxo-5-n-propyl-1H,9H-benzopyrano[2,3-d]-v-triazole

To a solution of ethane thiol (10.2 g, 12.05 ml, 0.16 mole) in dry DMF (200 ml) was added a 50% dispersion of sodium hydride in mineral oil (7.65 g, 0.16 mole) and the mixture was stirred for 15 minutes at ambient temperature to complete formation of the sodium salt. Finely powdered 8-methoxy-9-oxo-5-n-propyl-1H,9H-benzopyrano[2,3-d]-v-triazole (5.66 g, 0.022 mole) was added in one portion and the total was stirred at 120° C. (oil bath temperature) for 1 hour. The DMF was removed in vacuo and water (250 ml) was added to the residue. After washing the resulting solution with ether the solution was cooled to 0° C. and acidified. The precipitated oil crystallized on trituration to give a yellow solid of tlc purity which was filtered off, washed with water and dried to give 5.09 g (95%) of the title compound of mp 208°-9° C. (dec) (from ethyl acetate).

$\nu_{max}$ (mull): 3130 (broad), 1650, 1638, 1618, 1560, 1525 cm$^{-1}$.

δ (DMSO-d₆): 0.95 (3H, t, J 7.2 Hz); 1.68 (2H, sextet, J 7 Hz); 2.78 (3H, t, J 7 Hz); 6.82 (1H, d, J 8 Hz); 7.62 (1H, d, J 8 Hz); 12.24 (1H, sharp exchangeable s); 15.2 (1H, broad exchangeable).

(Found: C, 59.08; H, 4.41; N, 16.83. C₁₂H₁₁N₃O₃ requires: C, 58.77; H, 4.52; N, 17.14%)

(f)

8-Hydroxy-9-oxo-5-n-propyl-2-(triphenylmethyl)-9H-benzopyrano[2,3-d]-v-triazole

Anhydrous potassium carbonate (1.04 g) and triphenylmethyl chloride (1.39 g, 5 mmole) were added to a solution of 8-hydroxy-9-oxo-5-n-propyl-1H,9H-benzopyrano[2,3-d]-v-triazole (1.23 g, 5 mmole) in dry DMF (50 ml) and the mixture was stirred at 60° C. for 18 hours. After cooling the solvent was removed in vacuo and water added. After bringing the pH to 6 with hydrochloric acid the yellow solid was filtered off and dried to give 2.26 g of crude title compound. Chromatography on silica eluting with dichloromethane gave 1.60 g (69%) of title compound as a yellow solid, mp (ethanol-chloroform) 194°-5° C.

ν$_{max}$ (mull): 1662, 1625, 1550 cm⁻¹.

δ (CDCl₃): 0.98 (3H, t, J 7.2 Hz); 1.66 (2H, sextet, J 7.2 Hz); 2.77 (2H, t, J 7.2 Hz); 6.82 (1H, d, J 8 Hz); 7.3 (15H, m); 7.48 (1H, d, J 8 Hz); 12.33 (1H, sharp exchangeable s).

(Found: C, 74.85; H, 5.46; N, 8.27. C₃₁H₂₅N₃O₃.0.5-H₂O requires: C, 74.98; H, 5.78; N, 8.46%)

From the aqueous phase was obtained 0.36 g of starting phenol by acidification to pH 1.

(g)

8-[3-(4-Acetyl-3-hydroxy-2-n-propylphenoxy)propan-1-yloxy]-9-oxo-5-n-propyl-2-(triphenylmethyl)-9H-benzopyrano[2,3-d]-v-triazole Triphenylphosphine (1.07 g) was added to a solution of 8-hydroxy-9-oxo-5-n-propyl-2-(triphenylmethyl)-9H-benzopyrano[2,3-d]-v-triazole (0.974 g, 2 mmole) and 3-(4-acetyl-3-hydroxy-2-n-propylphenoxy)propan-1-ol (0.47 g, 2 mmole) in dry tetrahydrofuran (60 ml) and a solution of diethyl azodicarboxylate (0.71 g) in THF (2 ml) was added. After stirring for 1 hour at ambient temperature the solvent was evaporated and the residue was chromatographed on 50 g of silica gel eluting with dichloromethane to give 0.25 g (17%) of title compound as a foam.

δ (CDCl₃): 0.87 (3H, t, J 6 Hz); 0.92 (3H, t, J 6 Hz); 1.54 (4H, m); 2.32 (2H, t, J 6 Hz); 2.47 (3H, s); 2.67 (4H, m); 4.23 (2H, t, J 6 Hz); 4.42 (2H, t, J 6 Hz); 6.54 (1H, d, J 9 Hz); 6.75 (1H, d, J 9 Hz); 7.30 (15H, m); 7.38 (1H, d, J 9 Hz); 7.52 (1H, d, J 9 Hz); 12.77 (1H, sharp exchangeable s).

EXAMPLE 7

8-[3-(4-Acetyl-3-hydroxy-2-n-propylphenoxy)-propan-1-yloxy]-9-oxo-5-n-propyl-1H,9H-benzopyrano[2,3-d]-v-triazole

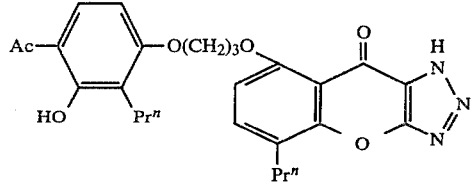

Concentrated hydrochloric acid (0.30 ml) was added to a solution of 8-[3-(4-acetyl-3-hydroxy-2-n-propylphenoxy)propan-1-yloxy]-9-oxo-5-n-propyl-2-(triphenylmethyl)-9H-benzopyrano[2,3-d]-v-triazole (0.14 g) in glacial acetic acid (10 ml) and the mixture was stirred at 70° C. for 2 hours. The cooled solution was evaporated to a white solid which was triturated with water, separated and dried. Chromatography on silica gel eluting with dichloromethane, chloroform and finally 10% methanol in chloroform afforded 87 mg (94%) of the title compound of mp (ethanol) 207°-8° C.

ν$_{max}$ (mull): 1650, 1635, 1595, 1550 cm⁻¹.

δ (DMSO-d₆): 0.75 (3H, t, J 6 Hz); 0.90 (3H, t, J 6 Hz); 1.47 (4H, complex m); 2.23 (2H, t, J 6 Hz); 2.43 (2H, m); 2.52 (3H, s); 2.76 (2H, t, J 7.5 Hz); 4.20 (2H, t, J 6 Hz); 4.42 (2H, t, J 6 Hz); 6.70 (1H, d, J 9 Hz); 6.98 (1H, d, J 8 Hz); 7.60 (1H, d, J 8 Hz); 7.77 (1H, d, J 8 Hz); 12.8 (1H, s).

Found: C, 64.99; H, 5.92; N, 8.53. C₂₆H₂₉N₃O₆ requires: C, 65.12; H, 6.10; N, 8.76%.

DESCRIPTION 8

(a)

6-Hydroxy-N-(4-methoxybenzyl)-9-oxo-5-n-propyl-9H-benzopyrano-[2,3-d]-v-triazole 6-Hydroxy-9-oxo-5-n-propyl-1H,9H-benzopyrano[2,3-d]-v-triazole (1.0 g, 4.0 mmole) (prepared as in Description 6(f)) was dissolved in dry DMF (40 ml) and treated with anhydrous potassium carbonate (0.83 g, 6.0 mmole) and 4-methoxybenzylchloride (0.64 g, 4.0 mmole). The mixture was stirred at room temperature for 18 hours after which time the solvent was removed in vacuo. The residue was acidified with 5 M hydrochloric acid, and extracted with ethyl acetate. The organic phase was washed with water, brine and dried (MgSO₄). After evaporation of the solvent the resulting oil was chromatographed to give 1.29 g (88%) of mixing isomers believed to be the N-1 and N-2 derivatives and 64 mg (4%) of N-3 isomer. A pure sample of the N-2 isomer was obtained from the column.

N-2 Isomer mp (MeOH) 194° C.

ν$_{max}$ (mull) 1598, 1615, 1650, 1665, 3120 cm⁻¹.

δ DMSO-d₆: 0.95 (3H, t, J 7 Hz); 1.59 (2H, m); 2.70 (2H, m); 3.78 (3H, s); 5.73 (2H, s); 7.02 (1H, d, J 9 Hz); 7.22 (4H, ABq, Δν=40.5 Hz J 9 Hz); 7.94 (1H, d, J 9 Hz); 10.92 (1H, s).

Found: C, 65.54; H, 5.25; N, 11.23. (C₂₀H₁₉N₃O₄ requires: C, 65.74; H, 5.24; N, 11.50%)

M⁺=365.1370 (C₂₀H₁₉N₃O₄).

N-3 Isomer mp (MeOH) 210-1° C.

ν$_{max}$ (mull): 1595, 1615, 1663, 3140 cm⁻¹.

δ DMSO-d6: 0.88 (3H, t, J 7 Hz); 1.46 (2H, m); 2.70 (2H, t, J 7 Hz); 3.73 (3H, s); 5.72 (2H, s); 6.98 (1H, d, J 9 Hz); 7.15 (4H, ABq, Δν=40.5 Hz, J 9 Hz); 7.94 (1H, d, J 9 Hz); 10.88 (1H, s).

Found: C, 65.72; H, 5.32; N, 11.29 ($C_{20}H_{19}N_3O_4$ requires C, 65.74; H, 5.24; N, 11.50%).

$M^+ = 365.1373$ ($C_{20}H_{19}N_3O_4$).

(b)
6-[3-(4-Acetyl-3-hydroxy-2-n-propylphenoxy)-2-hydroxy-propan-1-yloxy]-N-(4-methoxybenzyl)-9-oxo-5-n-propyl-9H-benzopyrano[2,3-d]-v-triazole A solution of the above mixed isomers, N-1 and N-2 (0.894 g, 2.5 mmole) and 4-(2,3-epoxypropoxy)-2-hydroxy-3-n-propyl-acetophenone (0.734 g, 5.0 mmole) in dry DMF (40 ml) was treated with 'Triton B' (5 drops) and the solution stirred at reflux temperature for 24 hours. Tlc showed the reaction was complete. On cooling the solvent was evaporated in vacuo and the brown residue partitioned between ethyl acetate and water. The organic phase was separated, dried (MgSO4) and evaporated in vacuo to yield a brown oil. Purification with column chromatography using silica gel eluting $CH_2Cl_2 \rightarrow CHCl_3$ yielded 0.959 (63%) of mixed isomers. Pure N-1 isomer could be separated by further chromatography.

Data N-1 isomer, mp (ethanol/water) 83-5° C.
$\nu_{max}$ (mull): 1616, shoulder at 1630, 1670 cm$^{-1}$.
δ (DMSO-d6): 0.87 (6H, 2t, J 7 Hz); 1.50 (4H, m); CH2 obscured by DMSO at 2.50; 2.57 (3H, s); 3.29 (2H, m); 3.72 (3H, s); 4.30 (5H, m); 5.54 (1H, bs, exchanged D2O); 5.90 (2H, s); 6.69 (1H, d, J 9 Hz); 7.16 (4H, ABq, Δν=38 Hz, J 9 Hz); 1H obscured by ABq; 7.82 (1H, J 9 Hz); 7.12 (1H, d, J 9 Hz); 12.80 (1H, s, exchanged D2O).

(c)
6-[3-(4-Acetyl-3-hydroxy-2-n-propylphenoxy)-2-hydroxypropan-1-yloxy]-9-oxo-5-n-propyl-1H,9H-benzopyrano-[2,3-d]-v-triazole

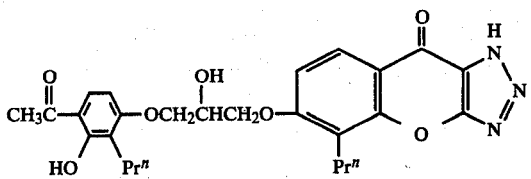

A solution of the above isomers (0.85 g) in trifluoroacetic acid (20 ml) was heated with stirring at 65° C. for 3.5 hours. Tlc showed no starting material. The brown solution was cooled and evaporated in vacuo to dryness. The residue was suspended in water and basified to pH 9 with 1 M sodium hydroxide solution stirred for 0.5 hr, then re-acidified to pH 6 with dilute acetic acid and extracted with ethyl acetate. The organic phase was separated, washed with water, brine and dried (MgSO4). Evaporation in vacuo yielded a green foam which was purified by column chromatography using silica gel, eluting with $CH_2Cl_2 \rightarrow CHCl_3/10\%$ MeOH to yield pure product. Recrystallised from methanol/water to yield 287 mg (42%) of pale cream crystals, mp 92-3° C. (dec).

$\nu_{max}$ (mull): 1560, 1618, shoulder at 1625, 1665 (weak) cm$^{-1}$.

δ (DMSO-d6): 0.77 (3H, t, J 7 Hz); 0.87 (3H, t, J 7 Hz); 1.47 (4H, m); 2.50 (2H, m, obscured); 2.57 (3H, s); 285 (2H, m); 4.30 (5H, m); 5.53 (1H, s, exchanged D2O); 6.69 (1H, d, J 9 Hz); 7.27 (1H, d, J 9 Hz); 7.82 (1H, d, J 9 Hz); 8.11 (1H, d, J 9 Hz); 12.79 (1H, s, exchanged D2O).

Found: C, 62.87; H, 5.79; N, 8.25 ($C_{26}H_{29}N_3O_7$ requires C, 63.04; H, 5.90; N, 8.48%).

6-[3-(4-Acetyl-3-hydroxy-2-n-propylphenoxy)-2-hydroxypropan-1-yloxy]-9-oxo-5-n-propyl-9H-benzopyrano-[2,3-d]-v-triazole mono-sodium salt A solution of the above compound (230 mg) in aqueous ethanol was basified with standard 0.1 M sodium hydroxide solution (0.38 ml) to pH 8. The solution was evaporated in vacuo to near dryness and the residual oil triturated with diethyl ether to yield 144 mg (60%) of product, mp 155-7° C. (dec).

$\nu_{max}$ (mull): 1550, 1610, 1637 cm$^{-1}$.

δ DMSO-d6: 0.75 (3H, t, J 7 Hz); 0.85 (3H, t, J 7 Hz); 1.46 (4H, m); 2.50 (2H, m, obscured by DMSO); 2.58 (3H, s); 3.27 (2H, t, J 7 Hz); 4.26 (5H, bs); 5.50 (1H, s, exchanged D2O); 6.68 (1H, d, J 9 Hz); 7.08 (1H, d, J 9 Hz); 7.83 (1H, d, J 9 Hz); 8.03 (1H, d, J 9 Hz); 12.86 (1H, s, exchanged D2O).

PHARMACOLOGICAL DATA SECTION

Activities in biological test systems

The compounds were tested for their ability to:
(a) inhibit rat passive peritoneal anaphylaxis; and
(b) antagonise the spasmogenic effects of slow reacting substance of anaphylaxis, SRS-A, on isolated guinea pig ileum.

The methods used are described below.

The compounds were used in the form of their sodium salts.

Animals

Charles River Sprague Dawley male rats of 250-300 g. and Dunkin Hartley male white guinea pigs of 250-300 g. were used.

Rat Passive Peritoneal Anaphylaxis (PPA)

The method has been described previously. (Ross, Janet W., Smith, H. and Spicer, Barbara A. Increased vascular permeability during passive peritoneal anaphylaxis in the rate. Int. Arch. Allergy appl. Immun., 51, 226, 1976).

Antiserum

Rats were sensitised by giving an intraperitoneal injection of 0.5 ml of Bordetella pertussis vaccine (4×10$^{10}$ organisms/ml Burroughs Wellcome, London) and a subcutaneous injection of 0.5 ml of an emulsion of 100 mg of ovalbumin (chicken egg albumin, crystallised and lyophilised, grade 3, Sigma, London) in 2 ml of isotonic saline and 3 ml of Freund's incomplete adjuvant (Difco Laboratories, Michigan, USA).

The rats were bled by cardiac puncture, on day 18, the blood was pooled, and the serum separated, stored at $-20°$ C. and thawed only once before use. The serum was shown to contain immunoglobulin E (IgE) antibody by its ability to sensitise rats for passive cutaneous anaphylaxis (carried out as described: Spicer, Barbara A; Ross, Janet W., and Smith, H; Inhibition of immediate hypersensitivity reactions in the rat by disodium cromoglycate and a nitroindanedione, Clin. exp., Immunol., 21, 419 1975) to a dilution of 1:32 to 1:64 persisting for at least 72 hours after sensitisation.

Passive peritoneal anaphylaxis

Rats were each given an intraperitoneal injection of 2 ml of a 1 in 5 dilution of the rat anti-serum in isotonic saline. Two hours later 0.3 ml of a 5% solution of Pontamine Sky Blue (Raymond A. Lamb, London) in isotonic saline was injected intravenously, followed by an intraperitoneal injection of the test compound in 1 ml of saline; (control rats received 1 ml of saline); followed 30 seconds later by an intraperitoneal injection of 5 ml of Tyrode's solution containing 50 µg/ml heparin and 0.4 mg/ml of ovalbumin. The concentrations of the compounds are quoted as those in the 6 ml of fluid injected intraperitoneally. Exactly five minutes after challenge the rats were stunned and bled and their peritoneal fluids were collected by opening their peritoneal cavities over funnels into polycarbonate tubes in ice. The supernatants were separated from the cellular residue by centrifugation at 150 g. for five minutes and were retained for assay of dye and histamine. Any samples obviously contaminated with blood were not used for estimation of dye. Groups of at least five rats were used for each dose of compound and the treatments were randomised.

Assay of peritoneal fluids

Dye was assayed within two hours by measurement of optical density (OD) at 625 nm.

For histamine assay 0.5 ml samples of the supernatants were added to 1 ml volumes of 12% trichloracetic acid and stored at $-20°$ C. The deproteinised samples were assayed using an automated spectrofluorimetric system (Technicon Autoanalyser) by a method similar to that of Evans, D. P., Lewis, J. A. and Thomson, D. S.: (An automated fluorimetric assay for the rapid determination of histamine in biological fluids. Life Sci., 12, 327, 1973). At the concentrations used the compounds tested did not interfere with the assay.

SRS-A Antagonist Activity

The compounds were evaluated as direct antagonists of slow reacting substance of anaphylaxis (SRS-A) by assay using the isolated guinea pig ileum.

SRS-A rat was obtained from the peritoneal cavity of the rat after passive peritoneal anaphylaxis by a method based on that of R. P. Orange, D. J. Stechschulte and K. F. Austen, J. Immunology, 105, 1087 (1970) as described by J. W. Ross, H. Smith and B. A. Spicer 1976, Increased vascular permeability during passive peritoneal anaphylaxis in the rat. Int. Arch. Allergy appl., 51, 226. The sensitising serum containing antibody was produced in rats as described by J. W. Ross et. al., ibid.

2 ml of a 1 in 5 dilution of the sensitising serum was injected by the peritoneal route into recipient rats and after 2 hours 5 ml of Tyrode's solution containing 0.4 mg/ml ovalbumin (Sigma Grade III) and 50 µg/ml heparin was injected by the same route. Five minutes after challenge the rats were stunned and bled and the peritoneal fluids collected into polycarbonate tubes in ice. After centrifugation at 150 g. for five minutes the supernatants were combined, heated in a boiling water bath for five minutes, cooled and stored at $-20°$ C. The combined peritoneal fluids contained SRS-A and were used in the antagonism studies.

The SRS-A assays were carried out on isolated strips of guinea pig ileum in Tyrode's solution containing atropine $5\times10^{-7}$ M and mepyramine $10^{-6}$ M as described by W. E. Brocklehurst, J. Physiology, 151, 416 (1960).

The ability of the antagonists was determined by their ability to reduce submaximal responses induced by SRS-A. The antagonists were added to the 4 ml bath in 0.1 ml volumes in aqueous solution half a minute before the addition of SRS-A and were present during induced contraction.

Results

The results obtained in these tests, which are shown in the following Tables demonstrate the ability of the compounds not only to inhibit the release of mediator substances but also to antagonise the effects of released SRS-A.

ACTIVITIES OF COMPOUNDS IN RAT PPA

| Example | Conc$^n$ injected ip (M) | Concentration in peritoneal fluid as % of mean of controls (Mean ± SEM, 5–7 rats per group) | |
|---|---|---|---|
| | | Histamine | Dye |
| 1 | $2 \times 10^{-5}$ | 17 ± 2 | 54 ± 7 |
|   | $2 \times 10^{-6}$ | 18 ± 2 | 63 ± 5 |
| 2 | $2 \times 10^{-6}$ | 14 ± 2 | 42 ± 5 |
|   | $2 \times 10^{-7}$ | 56 ± 1 | 61 ± 7 |
| 3 | $2 \times 10^{-6}$ | 16 ± 2 | 51 ± 5 |
|   | $2 \times 10^{-7}$ | 56 ± 5 | 74 ± 9 |
| 4 | $2 \times 10^{-5}$ | 42 ± 6 | 92 ± 10 |
|   | $2 \times 10^{-6}$ | 89 ± 7 | 104 ± 20 |

RESULTS

| Example | SRS-A Antagonism on Guinea Pig Ileum Approximate concentration to give a 50% inhibition of a less than maximal response to SRS-A |
|---|---|
| 1 | $1 \times 10^{-7}$ M |
| 2 | $3.2 \times 10^{-8}$ M |
| 3 | $6.3 \times 10^{-8}$ M |
| 4 | $5 \times 10^{-8}$ M |

Toxicity

No toxic effects were observed in these tests.

We claim:

1. A compound of formula (I):

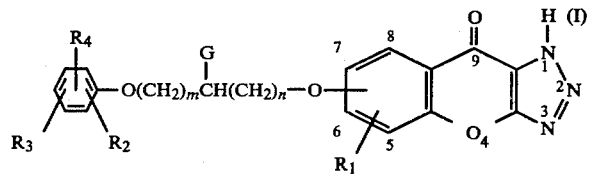

or a pharmaceutically acceptable salt thereof, wherein $R_1$ is hydrogen or $C_{1-6}$ alkyl;

$R_2$, $R_3$ and $R_4$ are the same or different and are chosen from hydrogen, hydroxyl, halogen, $C_{1-4}$ alkyl, $C_{1-4}$ alkoxy and $C_{1-4}$ alkanoyl;

G is H or OH; and m and n are independently 1 to 3; with the proviso that when G is OH, one of m and n is 1.

2. A compound according to claim 1, of the formula (V):

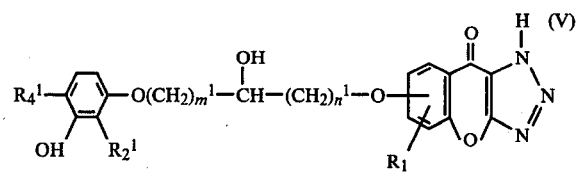

wherein
R$_1$ is hydrogen or C$_{1-6}$ alkyl;
m' and n' are independently 1 or 2;
R$^1_2$ is C$_{1-4}$ alkyl; and
R$^1_4$ is C$_{1-4}$ alkanoyl.

3. A compound according to claim 2, wherein R$^1_2$ is n-propyl and R$^1_4$ is acetyl.

4. A compound according to claim 2 wherein the side chain substitutes the benzo moiety at the 6-position.

5. A compound according to claim 2, wherein R$_1$ is H, 5-methyl or 5-n-propyl.

6. 6-[3-(4-Acetyl-3-hydroxy-2-n-propylphenoxy)-2-hydroxypropan-1-yloxy]-9-oxo-1H,9H-benzopyrano[2,3-d]-v-triazole or a pharmaceutically acceptable salt thereof.

7. 6-[3-(4-Acetyl-3-hydroxy-2-n-propylphenoxy)-2-hydroxypropan-1-yloxy]-5-methyl-9-oxo-1H,9H-benzopyrano[2,3-d]-v-triazole or a pharmaceutically acceptable salt thereof.

8. 6-[3-(4-Acetyl-3-hydroxy-2-n-propylphenoxy)-2-hydroxypropan-1-yloxy]-5-n-propyl-9-oxo-1H,9H-benzopyrano[2,3-d]-v-triazole or a pharmaceutically acceptable salt thereof.

9. The sodium salt of a compound according to claim 7.

10. A pharmaceutical composition having anti-allergic activity comprising an anti-allergic effective amount of a compound according to, claim 1 and a pharmaceutically acceptable carrier.

11. A method for the treatment of allergies, which method comprises administering to an allergy sufferer an effective amount of a compound of claim 1.

* * * * *